United States Patent
Johnson

(10) Patent No.: US 9,981,054 B2
(45) Date of Patent: May 29, 2018

(54) CIRCUIT LOOPS TO CONTROL FLUIDS

(71) Applicant: Qlean Tech IP, LLC, Mendota Heights, MN (US)

(72) Inventor: Thomas Johnson, Mendota Heights, MN (US)

(73) Assignee: QLEAN TECH IP, LLC, Mendota Heights, MN (US)

( * ) Notice: Subject to any disclaimer, the term of this patent is extended or adjusted under 35 U.S.C. 154(b) by 0 days. days.

(21) Appl. No.: 15/581,451

(22) Filed: Apr. 28, 2017

(65) Prior Publication Data

US 2017/0255209 A1 Sep. 7, 2017

Related U.S. Application Data

(63) Continuation of application No. PCT/US2016/053928, filed on Sep. 27, 2016.

(Continued)

(51) Int. Cl.
*A61L 2/18* (2006.01)
*G05D 7/06* (2006.01)
(Continued)

(52) U.S. Cl.
CPC .................. *A61L 2/18* (2013.01); *B08B 3/08* (2013.01); *G05B 15/02* (2013.01); *G05D 7/0641* (2013.01);
(Continued)

(58) Field of Classification Search
CPC ....... Y10T 137/2509; Y10T 137/86027; Y10T 137/4252; A61L 2/18; B08B 3/08; G05B 15/02; G05D 7/0641

(Continued)

(56) References Cited

U.S. PATENT DOCUMENTS 4,710,233 A 12/1987 Hohmann et al.
5,759,489 A * 6/1998 Miura ........................ A61L 2/18
134/22.11

(Continued)

FOREIGN PATENT DOCUMENTS

WO WO-2017058772 A1 4/2017

OTHER PUBLICATIONS

"U.S. Appl. No. 15/646,694, Response filed Nov. 21, 2017 to Restriction Requirement dated Sep. 26, 2017", 8 pgs.

(Continued)

*Primary Examiner* — William McCalister
(74) *Attorney, Agent, or Firm* — Schwegman Lundberg & Woessner, P.A.

(57) ABSTRACT

Discussed herein are systems, apparatuses, and methods for reversing a flow through a conduit loop. A system may include a flow reversing loop having an inlet, an outlet in communication with a drain, a first port on a first side of the flow reversing loop, and a second port on a second side of the flow reversing loop, the first and second sides separated by the inlet and outlet, a conduit loop including one or more flow paths, wherein the flow reversing loop includes a first flow path from the inlet to the first port so that the treatment fluid can flow through the conduit loop in a first direction to the outlet of the flow reversing loop, and a second flow path from the inlet to the second port so that the treatment fluid can flow to the drain in a second direction, opposite of the first direction.

10 Claims, 14 Drawing Sheets

Related U.S. Application Data

(60) Provisional application No. 62/233,462, filed on Sep. 28, 2015, provisional application No. 62/260,778, filed on Nov. 30, 2015, provisional application No. 62/299,100, filed on Feb. 24, 2016.

(51) Int. Cl.
  *B08B 3/08* (2006.01)
  *G05B 15/02* (2006.01)
(52) U.S. Cl.
  CPC .... *Y10T 137/2509* (2015.04); *Y10T 137/4252* (2015.04); *Y10T 137/86027* (2015.04)
(58) Field of Classification Search
  USPC ...................................... 137/93, 565.16, 239
  See application file for complete search history.

(56) References Cited

U.S. PATENT DOCUMENTS

| | | | | |
|---|---|---|---|---|
| 6,022,512 | A * | 2/2000 | Tanaka | A61L 2/18 134/166 C |
| 6,379,632 | B1 * | 4/2002 | Kinoshita | A61L 2/18 134/170 |
| 6,632,973 | B1 * | 10/2003 | Miyake | A62D 3/38 210/762 |
| 6,770,150 | B1 * | 8/2004 | Duckett | A61L 2/18 134/10 |
| 8,282,974 | B2 | 10/2012 | Johnson et al. | |
| 2004/0007255 | A1 * | 1/2004 | Labib | A61L 2/18 134/30 |
| 2004/0156744 | A9 | 8/2004 | Stanley | |
| 2007/0214815 | A1 | 9/2007 | Lewkowitz et al. | |
| 2009/0236235 | A1 | 9/2009 | Wilkins et al. | |
| 2010/0252074 | A1 * | 10/2010 | Sewake | A61B 1/123 134/19 |
| 2015/0246316 | A1 | 9/2015 | Chancellor | |
| 2017/0255209 | A1 * | 9/2017 | Johnson | G05D 7/0641 |

OTHER PUBLICATIONS

"U.S. Appl. No. 15/646,694, Restriction Requirement dated Sep. 26, 2017", 7 pgs.

Swan, J.S., et al., "Elimination of biofilm and microbial contamination reservoirs in hospital washbasin U-bends by automated cleaning and disinfection with electrochemically activated solutions", Journal of Hospital Infection 94.2, (2016), 169-174.

Second International Symposium: Electrochemical Activation in Medicine, Agriculture and Industry (Summaries of Papers and Breif Reports), Copyright © RSCECAT Int. Ltd., Technology Transfer Center, (1999), 491 pgs.

"Aquaox ECS Series", Aquaox Onsite Production of Electrolyzed Water, catalog/brochure, "To reduce chemicals and replace them with ecological friendly disinfectants", printed at least as early as Sep. 2, 2015., 1-6.

"Aquaox ECS Series", Aquaox Onsite Production of Electrolyzed Water, technical brochure, "To reduce chemicals and replace them with ecological friendly disinfectants", printed at least as early as Sep. 2, 2015, 1-6.

"International Application Serial No. PCT/US2016/053928, International Search Report dated Feb. 16, 2017", 4 pgs.

"International Application Serial No. PCT/US2016/053928, Invitation to Pay Add'l Fees and Partial Search Rpt dated Nov. 28, 2016", 3 pgs.

"International Application Serial No. PCT/US2016/053928, Written Opinion dated Feb. 16, 2017", 11 pgs.

Johnson, Thomas, "Evolved Sanitary Operations Platforms", Johnson Diversified Products, Inc., 46.

\* cited by examiner

US 9,981,054 B2

CIRCUIT LOOPS TO CONTROL FLUIDS

RELATED APPLICATIONS

This application is a continuation under 35 U.S.C. § 111(a) and claims benefit of priority to International Patent Application Serial No. PCT/US2016/053928, filed Sep. 27, 2016 and titled "CIRCUIT LOOPS TO CONTROL FLUIDS," which application claims the benefit of priority to U.S. Provisional Patent Application Ser. No. 62/233,462, filed Sep. 28, 2015 and titled "SYSTEMS AND METHODS FOR ANOLYTE AND CATHOLYTE STORAGE", U.S. Provisional Patent Application Ser. No. 62/260,778, filed Nov. 30, 2015 and titled "SYSTEMS AND METHODS FOR CLEANING AND SANITIZING SURFACES", and U.S. Provisional Patent Application Ser. No. 62/299,100, filed Feb. 24, 2016 and titled "CONDUIT MANIFOLDS AND CIRCUIT LOOPS TO PROVIDE CONTROL OF CONTINUOUSLY FLOWING FLUIDS", all of which are hereby incorporated by reference in their entirety.

TECHNICAL FIELD

Some embodiments discussed herein relate to devices, systems, and methods for production and storage of a cleaning agent (catholyte) and a sanitizing agent (anolyte).

Some embodiments discussed herein relate to cleaning and/or sanitizing surfaces.

Some embodiments discussed herein relate to conduit manifolds and fluid sub-loops to provide reversible/continuous flow of fluids, such as through multiple stories of the same building.

Some embodiments discussed herein relate to devices, systems, and methods for providing control of fluids (e.g., continuously flowing fluids). One or more embodiments regard sanitizing a conduit using a conduit and valve system configured to provide fluid flow in multiple directions in the same conduit.

TECHNICAL BACKGROUND

Many entities use toxic chemicals for cleaning and sanitization of their facilities and/or equipment. These toxic chemicals may be detrimental as the toxic chemicals may be ingested, their fumes inhaled, splattered into eyes, and discharged into the environment consuming oxygen in lakes rivers and streams causing environmental damage while killing and injuring flora and fauna. Patrons and personnel in facilities may come in contact with the toxic chemicals. The toxic chemicals may be detrimental to foodservice retailers as the toxic chemicals may get into the food or drinks that are served. In other industries, the patrons of the facilities may come in contact with the toxic chemicals.

It would be advantageous to identify a method for de-soiling and/or decontaminating environmental contact surfaces to a degree of cleanliness that the application of an approved sanitizer or disinfectant may reduce target pathogens below their infective dose. It may be beneficial if the cleaner(s) used to decontaminate the surface were not antagonistic with the sanitizer(s) that are used after decontamination. It may also be beneficial if the cleaner(s) and sanitizer(s) did not leave an alkaline film residue behind after the diluent water evaporates. Alkaline residues promote colonization of biofilms by providing the basic surface film foundation upon which they adhere and find suitable habitat. Also, when alkaline residues from floor cleaning detergents are rewetted, there is a reduction of the coefficient of friction causing the floor to become slippery leading to slip/fall risks.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate, by way of example, but not by way of limitation, various embodiments discussed in the present document.

DESCRIPTION OF EMBODIMENTS

Systems and Methods for Anolyte and Catholyte Storage

One or more embodiments relate to producing anolyte and catholyte and storage of the same. The production of the anolyte and catholyte may be performed at or near a location at which the anolyte and/or catholyte are to be used.

Catholyte, a cleaner, and anolyte, a disinfectant and sanitizer, may be generated on-site by electrolysis of a dilute brine, and used in place of these toxic chemicals. Not only are catholyte and anolyte non-toxic and consumable, but they may be easily produced on-site at a facility using potable water, salt, and electricity.

Figure 1:
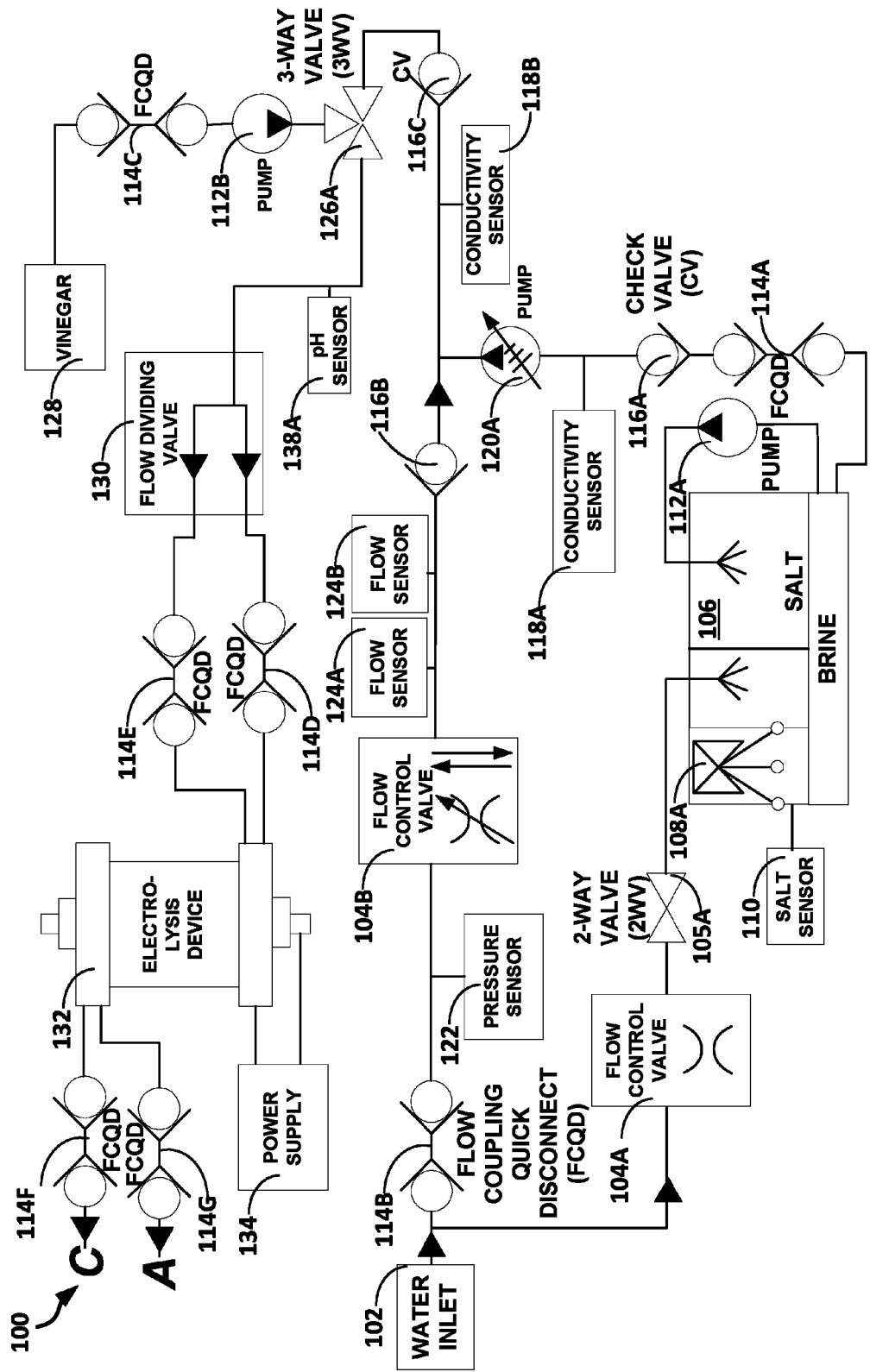
FIG. 1 illustrates, by way of example, a diagram of an embodiment of a portion of a system for production and storage of anolyte and catholyte.
Figure 2:
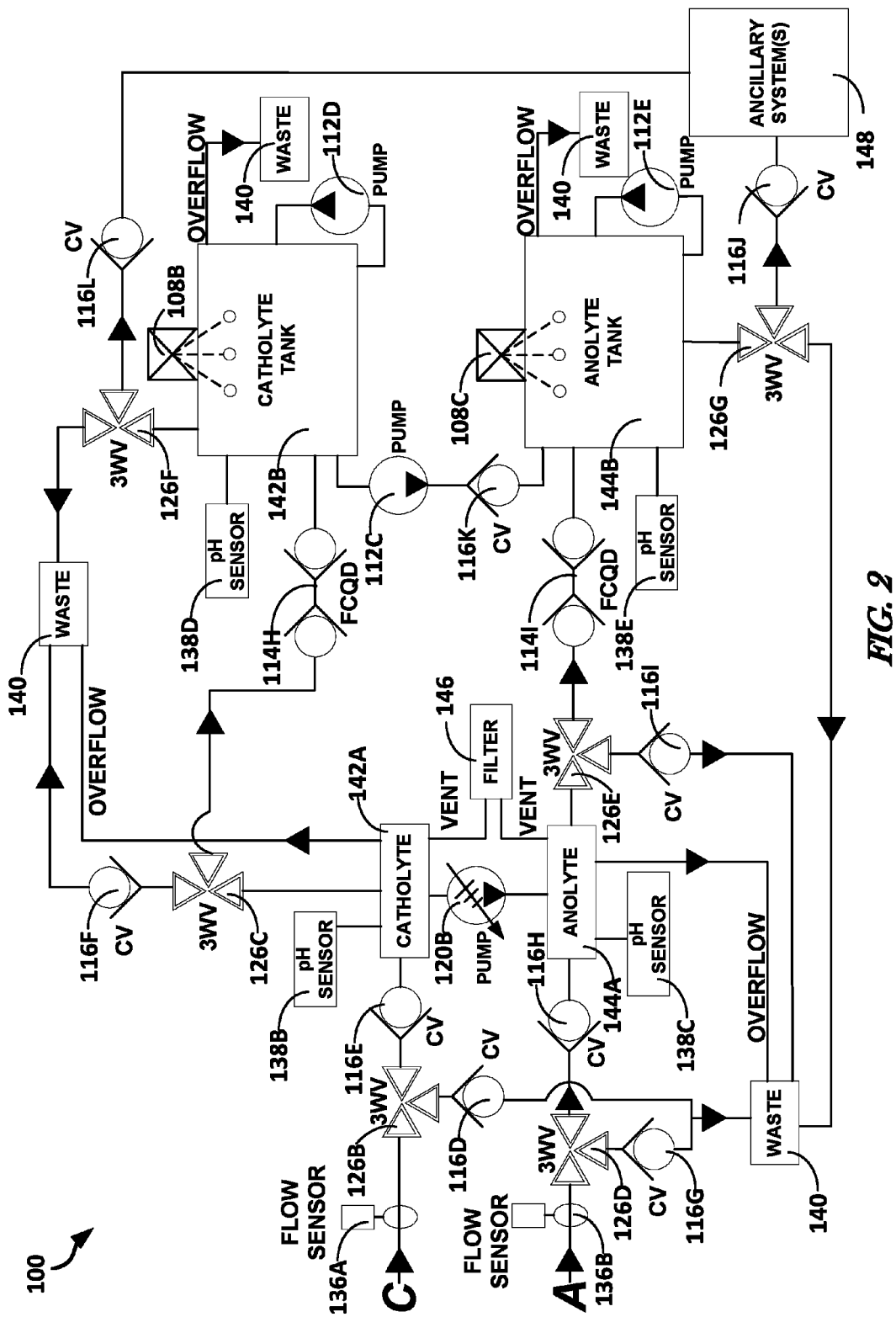
FIG. 2 illustrates, by way of example, a diagram of an embodiment of another portion of the system for production and storage of anolyte and catholyte.

FIG. 1 illustrates, by way of example, a diagram of an embodiment of a portion of a system 100 for production and storage of anolyte and catholyte. FIG. 2 illustrates, by way of example, an embodiment of another portion of the system 100 for production and storage of anolyte and catholyte. While the system 100 is illustrated as including number of check valves, Flow Coupling Quick Disconnects (FCQDs), sensors, flow control devices, valves (two and three-way valves, and receptacles (e.g., tanks, drains, containers, or the like), it will be apparent that not all items shown are required for an operational system, method, or device suitable for production and/or storage of anolyte and catholyte.

The system 100 as illustrated includes a water inlet 102. Water from the water inlet is in fluid communication with a flow control valve 104A and an FCQD 114B. An FCQD is used to connect or disconnect a hydraulic line which is coupled to the water inlet 102. The FCQD may be a non-spill single or double shut-off quick coupling and/or a connector that may be connected or disconnected under pressure.

The water from the water inlet 102, in one or more embodiments is reverse osmosis water. In one or more embodiments, the water from the water inlet 102 includes less than one part per million (ppm) of each of hardness, fluoride, iron, magnesium, and borax and borate. In one or more embodiments, a flow rate of the water from the water inlet 102 is between about 22-30 gallons per hour. In one or more embodiments, the water from the water inlet is at a pressure of about forty-five to fifty pounds per square inch (psi).

A flow control valve regulates a flow or pressure of water from the water inlet 102. The flow or pressure may be specified according to the application. In one or more embodiments, the flow control valve regulates the flow or pressure of the water to a specified pressure. A two-way valve (2WV) 105A is in fluid communication with fluid from the flow control valve 104A and a tank 106. The 2WV 105A, when open, provides a path for water to flow to the tank 106. When closed, the 2WV 105A prevents water from flowing to the tank 106.

A salt sensor 110 is in fluid communication with liquid in the tank 106. The salt sensor 110, sometimes also called a salinity sensor, provides an indication of how much salt is dissolved in the liquid in the tank 106. The water from the 2WV 105A and salt in the tank 106, such as may be manually placed in the tank 106, mix to create a brine solution in the tank 106. The salt sensor 110 determines how much salt is in the brine solution. A pump 112A is in fluid communication with brine in the tank 106 and the salt of the tank 106. The pump 112A recirculates the brine over the salt, such as to increase the salt content of the brine. This recirculation helps ensure that the brine is completely saturated with salt. Such saturation helps provide a solution that is suitable for electrolysis, such as to produce catholyte and anolyte of a specified quality. In one or more embodiments, the pump 112A is a fixed displacement pump and in other embodiments, the pump is a variable displacement pump. In one or more embodiments, the pump 112A may be replaced with an agitator that may stir or otherwise circulate the brine over the salt in the tank 106.

In one or more embodiments, the tank 106 includes a level sensor 108A to control the water level in a well of the tank 106. An output of the level sensor 108A may be provided to the flow control valve 104A, such that the flow control valve 104A may be closed in response to determining the water in the well is greater than or equal a threshold level or the flow control valve 104A may be opened in response to determining the water in the well is less than the threshold level of water. The wall separating the water well from the salt may be perforated allowing the water to mix with the salt and produce the brine. The pump 112A may be similar to a pump used to circulate liquid in a fish tank. The pump 112A circulates brine over the salt. This helps ensure that the brine drawn into the machine is fully saturated, such as to help ensure constant electrical conductivity for the brine, which is directly correlated to the anolyte and catholyte produced by an electrolysis device 132 that uses the brine as an input.

An FCQD 114A is in fluid communication with the brine solution from the tank 106 and a check valve (CV) 116A. A check valve is a one-way valve that allows fluid flow in only one direction (the direction opposite the direction the arrow portion of the CV symbol is pointing). The check valve 116A allows the brine from the tank to flow therethrough to a dosing pump 120A and prevents fluid from flowing from the pump 120A to the FCQD 114A or back to the tank 106.

A conductivity sensor 118A is in fluid communication with liquid from the CV 116A and a dosing pump 120A. A conductivity sensor determines conductivity of an aqueous solution. The conductivity may be useful for determining a concentration of dissolved chemicals, such as the concentration of salt in the brine. Conductivity is a measure of a solution's ability to carry an electric current. Conductivity is the reciprocal of the resistance of a solution.

A dosing pump is a device that moves liquid with a controllable discharge rate. The dosing pump 120A is used to provide brine solution to water that passes through a CV 116B. A dosing pump may have a controller which enables the fluid flow from the pump to be monitored and adjusted (e.g., automatically, which means without human interference after deployment).

The FCQD 114B is in fluid communication with the water inlet 102 and a flow control valve 104B. A pressure sensor 122 is in fluid communication with liquid from the FCQD 114B. A pressure sensor determines how much force is required to stop a fluid from expanding and is expressed in force per unit area.

The flow control valve 104B is in fluid communication with water from the FCQD 114B. The flow control valve 104B, in one or more embodiments, may be a flow control valve that is pressure and temperature compensated. By compensating for temperature and pressure of the water from the water inlet 102 a more accurate regulation of the flow through the valve 104B may be realized.

A first flow sensor 124A and a redundant flow sensor 124B are in fluid communication with liquid from the flow control valve 104B. A flow sensor determines a volume of liquid displaced per unit time. Flow may be measured by determining a velocity of liquid over a known area or through a known volume. Alternatively, flow may be measured by determining forces produced by a flowing fluid as it overcomes a known constriction and inferring the flow rate based on the forces produced. The flow sensors 124A-B may perform the flow measurement in the same manner or different. The flow sensor 124B provides a redundant indication of the flow of the water from the flow control valve 104B. In most embodiments, the flow sensors 124A-B produce about the same measure of the flow rate of the liquid therethrough.

Another CV 116B is in fluid communication with liquid from the flow control valve 104B. Another conductivity sensor 118B and another CV 116C are in fluid communication with liquid from the check valve 116B and the dosing pump 120A. The water from the CV 116B mixes with the brine from the dosing pump 120A to produce a diluted brine solution. Thus, the conductivity of the liquid determined by the sensor 118B is, in most embodiments, less than the conductivity of the liquid determined by the sensor 118A.

A three-way valve (3WV) 126A is in fluid communication with liquid form the CV 116C and liquid from a pump 112B. A 3WV is a one valve, two flow pattern used to divert flow between two different flow paths. The 3WV 126A allows either the liquid from the CV 116C to flow therethrough or the liquid from the pump 112B (i.e. vinegar or other electrolysis device cleaning solution) to flow therethrough.

The pump 112B moves vinegar from a vinegar tank 128 through another FCQD 114C and to the 3WV. The FCQD 114C is in fluid communication with vinegar from the vinegar tank 128. The pump 112B is in fluid communication with vinegar from the tank 128.

A pH sensor 138A is in fluid communication with liquid from the 3WV 126A. A pH sensor measures a concentration or activity level of hydrogen ions in an aqueous solution. The data from a pH sensor indicates how acidic or basic a solution is.

A flow dividing valve 130 is in fluid communication with the 3WV 126A, another FCQD 114D, and another FCQD 114E. A flow dividing valve takes a fluid stream and splits it into multiple fluid streams. The flow dividing valve 130 receives liquid from the 3WV 126A and splits the liquid received into two streams. One stream is in fluid communication with an FCQD 114E and the other stream is in fluid communication with another FCQD 114D.

An electrolysis device 132 is in fluid communication with the FCQDs 114D-E, 114F and 114G. The electrolysis device 132 produces anolyte and catholyte from brine received from the flow dividing valve 130, such as through the FCQDs 114D-E. The electrolysis device 132 runs on electricity from a power supply 134. The power supply 134 is electrically coupled to the electrolysis device 132. A catholyte path is labelled "C" and an anolyte path is labelled "A". The two paths "C" and "A", as illustrated, may be symmetrical beyond the electrolysis device 132. Both lines from the electrolysis device 132 to the output at ancillary system(s) 148 include the same devices fluidly communicating in the same manner with a few exceptions including pumps 120B and 112C to introduce catholyte into anolyte tanks 144A and 144B, respectively. The remainder of the couplings and connections of the system 100 will be described with respect to the catholyte path ("C") and then with respect to the anolyte path ("A").

The FCQD 114F is in fluid communication with the electrolysis device 132. A flow sensor 136A is in fluid communication with liquid from the electrolysis device 132, such as through the FCQD 114F. The flow sensor 136 is similar to the flow sensor 124A-B with the flow sensor 136 as illustrated being an induction flow sensor. An induction flow sensor uses electromagnetic induction to determine a flow of an ionized solution. A magnetic field is applied to a tube carrying the liquid to be measured. A potential difference proportional to a flow velocity of the liquid in the tube is produced as a result. This potential difference is then mapped to a flow velocity to determine the flow rate of the liquid in the tube.

A 3WV 126B is in fluid communication with two CVs 116D and 116E and the catholyte from the electrolysis device 132, such as from the FCQD 114F. The 3WV 126B provides a path for liquids, such as vinegar or other electrolysis device cleaning solution, to be moved to a waste tank 140. The 3WV 126B provides another path for catholyte to be moved to a catholyte tank 142A, such as through the CV 116E.

The CV 116D is in fluid communication with the 3WV 126B and the waste tank 140. The waste tank 140 may be any receptacle, such as a container, drain, or other receptacle, to receive fluid from the system 100. The CV 116E is in fluid communication with the 3WV 126B and a catholyte tank 142A. A pH sensor 138B is in fluid communication with fluid in or from the catholyte tank 142A to monitor a pH of the catholyte in the catholyte tank 142A.

The tank 142A as illustrated includes an overflow valve (indicated by "OVERFLOW"). The overflow valve is in fluid communication with the waste tank 140. An overflow valve may be placed on a tank and set to an open position. The overflow valve may be placed at a location that allows a sufficient amount of liquid to be stored in the tank 142B while still allowing the valve to help prevent tank overflow.

A dosing pump 120B is in fluid communication with the catholyte tank 142A and the anolyte tank 144A. The dosing pump 120B provides catholyte from the catholyte tank 142A to help increase a pH of the anolyte in the anolyte tank 144A. A vent (indicated by "VENT") may be connected to the catholyte tank 142A, such as to receive a gas emitted from the catholyte tank 142A. The vent may guide the emitted gas to a filter 146. The filter 146 may be a carbon filter, ceramic filter, or other gas filter.

A 3WV 126C is in fluid communication with the catholyte tank 142A, a CV 116F, and an FCQD 114H. The 3WV provides a first path for catholyte from the catholyte tank 142A to be moved to another catholyte tank 142B and a second path for catholyte from the catholyte tank 142A to be moved to the waste tank 140. The path to the waste 140 may be selected (e.g., automatically) in response to determining that a level sensor 108B on the catholyte tank 142B indicates that the tank 142B is full. The path to the catholyte tank 142B may be selected (e.g., automatically) in response to determining that the level sensor 108B indicates that the tank 142B is not full (i.e. is below a threshold level to be detected by the sensor 108B). The catholyte from the tank 142A may be moved to the waste 140 or the tank 142B, such as by a pump (not shown in FIG. 2) or a gravity feed.

The CV 116F is in fluid communication with the 3WV 126C and the waste tank 140. The FCQD 114G is in fluid communication with the 3WV 126C and another catholyte tank 142B.

The catholyte tank 142B includes a level sensor 108B and an overflow valve (indicated by "OVERFLOW"). In one or more embodiments, the overflow valve may be set to open persistently, such as to help prevent the level of the liquid in the tank to reach a level higher than the overflow valve. In one or more embodiments, the overflow valve may be situated lower on the tank and may be switched open in response to a level sensor indicating that the tank includes more than a sufficient amount of fluid therein.

A recirculating pump 112D circulates catholyte in the tank 142B. A pump 112C is in fluid communication with the tank 142B and a CV 116K. The pump 112C moves catholyte from the catholyte tank 142B to the CV 116K. The CV 116K allows catholyte to pass to another anolyte tank 144B. A pH sensor 138D is in fluid communication with catholyte in or from the catholyte tank 142B.

A 3WV 126F is in fluid communication with the catholyte tank 142B, a waste tank 140, and a CV 116L. The 3WV 126F provides a path for catholyte from the catholyte tank 142B to be moved to the waste tank 140 and another path for catholyte from the catholyte tank 142B to be moved to ancillary system(s) 148. The CV 116L is in fluid communication with the 3WV 126F and an ancillary system(s) 148. The path to the waste 140 may be selected (e.g., automatically) in response to determining that the pH sensor 138D indicates that the catholyte in the tank 142B does not have a sufficient pH. The path to the ancillary system(s) 148 may be selected (e.g., automatically) in response to determining that the pH sensor 138D indicates that the catholyte in the tank 142B includes sufficient pH and an ancillary system 148 may use the catholyte. The catholyte may be pumped to the ancillary system 148, such as by a pump of the ancillary system 148 (pump not shown in FIG. 2).

The ancillary system 148 is a system that uses anolyte and/or catholyte in its operation. In one or more embodiments, the ancillary system is a washer, such as a dish washer, a bottle filling station, or other catholyte and/or anolyte dispenser. The ancillary system 148 is optional. In one or more embodiments that do not include the ancillary system 148, a user may manually remove catholyte from the catholyte tank 142B and/or remove anolyte from the anolyte tank 144B for cleaning and sanitizing, respectively.

The FCQD 114G is in fluid communication with anolyte from the electrolysis device 132. A flow sensor 136B is in fluid communication with liquid from the electrolysis device 132, such as through the FCQD 114G. The flow sensor 136B is similar to the flow sensor 136A.

A 3WV 126D is in fluid communication with two CVs 116G and 116H and the anolyte from the electrolysis device 132, such as from the FCQD 114G. The 3WV 126D provides a path for liquids, such as vinegar or other electrolysis device cleaning solution, to be moved to the waste tank 140. The 3WV 126B provides another path for anolyte to be moved to the anolyte tank 144A, such as through the CV 116H. The CV 116G is in fluid communication with the 3WV 126D and the waste tank 140. The CV 116H is in fluid communication with the 3WV 126D and the anolyte tank 144A. A pH sensor 138C is in fluid communication with fluid in or from the anolyte tank 144A to monitor a pH of the anolyte in the anolyte tank 144A.

A vent (indicated by "VENT") may be connected to the anolyte tank 144A, such as to receive a gas emitted from the anolyte tank 144A. The vent may guide the emitted gas to the filter 146.

A 3WV 126E is in fluid communication with the anolyte tank 144A, a CV 116I, and an FCQD 114I. The 3WV 126E provides a first path for anolyte from the anolyte tank 144A to be moved to another anolyte tank 144B and a second path for anolyte from the anolyte tank 144A to be moved to the waste tank 140. The path to the tank 140 may be selected (e.g., automatically) in response to determining that a level sensor 108C on the anolyte tank 144B indicates that the tank 144B includes liquid at or above a threshold level being monitored by the level sensor 108C. The path to the anolyte tank 144B may be selected (e.g., automatically) in response to determining that the level sensor 108C indicates that the tank 144B is not full (i.e. is below a threshold level to be detected by the sensor 108C). The anolyte from the tank 142A may be moved to the tank 140 or the tank 144B, such as by a pump (not shown in FIG. 2) or a gravity feed.

The CV 116I is in fluid communication with the 3WV 126E and the waste tank 140. The FCQD 114G is in fluid communication with the 3WV 126E and another anolyte tank 144B.

The anolyte tank 144B includes a level sensor 108C and an overflow valve (indicated by "OVERFLOW"). The overflow valve is in fluid communication with the waste tank 140. The tank 144B allows byproduct gases (e.g., chlorine and/or hydrogen) to be released from the anolyte solution.

A recirculating pump 112E circulates anolyte in the tank 142B. Anolyte or catholyte may degrade if not recirculated. Also, recirculation helps release the byproduct gases from the anolyte. A pH sensor 138E is in fluid communication with anolyte in or from the anolyte tank 144B, such as to monitor the pH of the anolyte.

A 3WV 126G is in fluid communication with the anolyte tank 144B, the waste tank 140, and a CV 116J. The 3WV 126G provides a path for anolyte from the anolyte tank 144B to be moved to the waste tank 140 and another path for anolyte from the anolyte tank 144B to be moved to ancillary system(s) 148. The CV 116I is in fluid communication with the 3WV 126G and the ancillary system(s) 148. The path to the waste 140 may be selected (e.g., automatically) in response to determining that the pH sensor 138E indicates that the anolyte in the tank 144B does not have a sufficient pH. The path to the ancillary system(s) 148 may be selected (e.g., automatically) in response to determining that the pH sensor 138E indicates that the anolyte in the tank 144B includes sufficient pH and an ancillary system 148 may use the anolyte. The anolyte may be pumped to the ancillary system 148, such as by a pump of the ancillary system 148 (pump not shown in FIG. 2).

Figure 3:
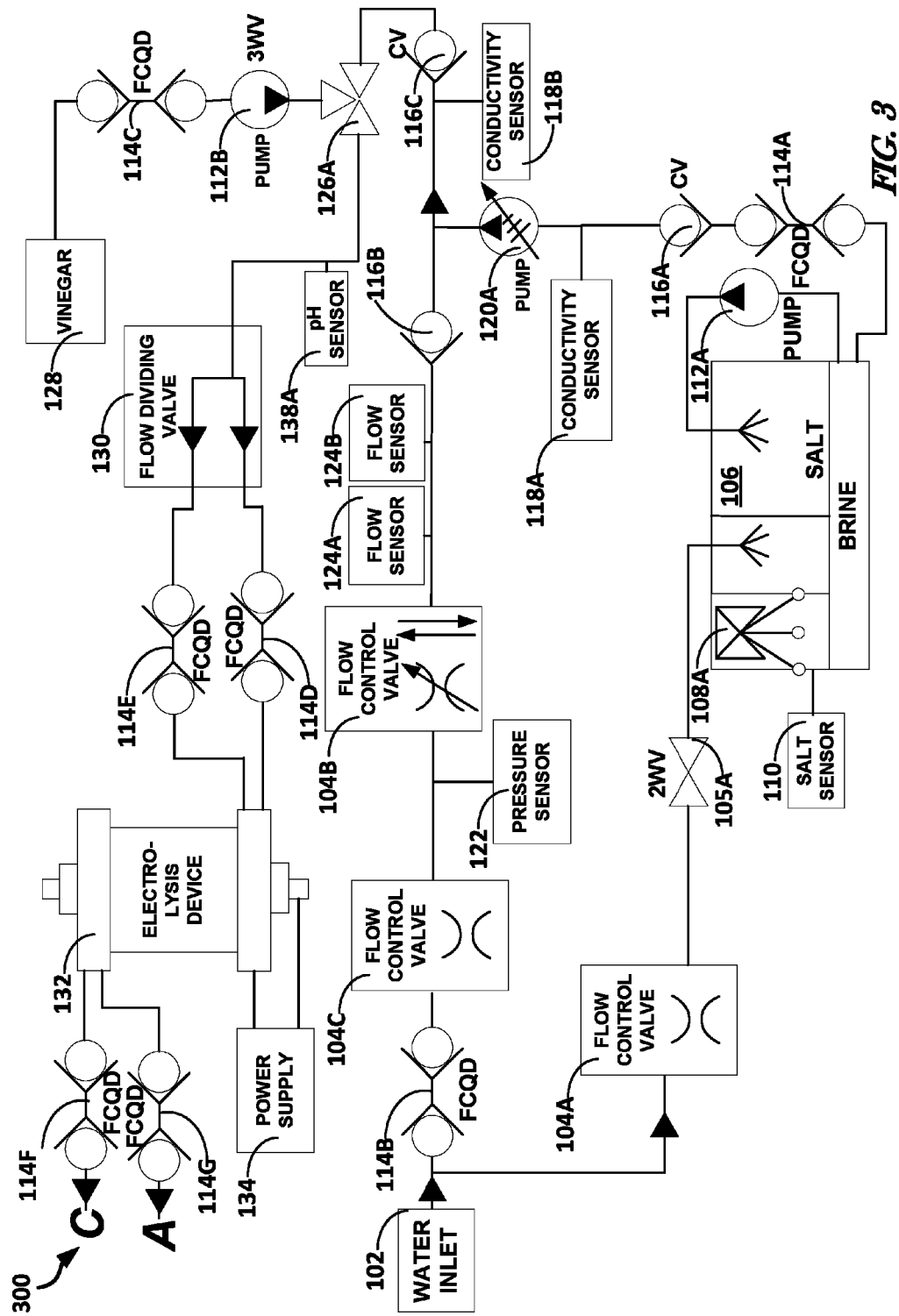
FIG. 3 illustrates, by way of example, a diagram of an embodiment of a portion of a system for production and storage of anolyte and catholyte.
Figure 4:
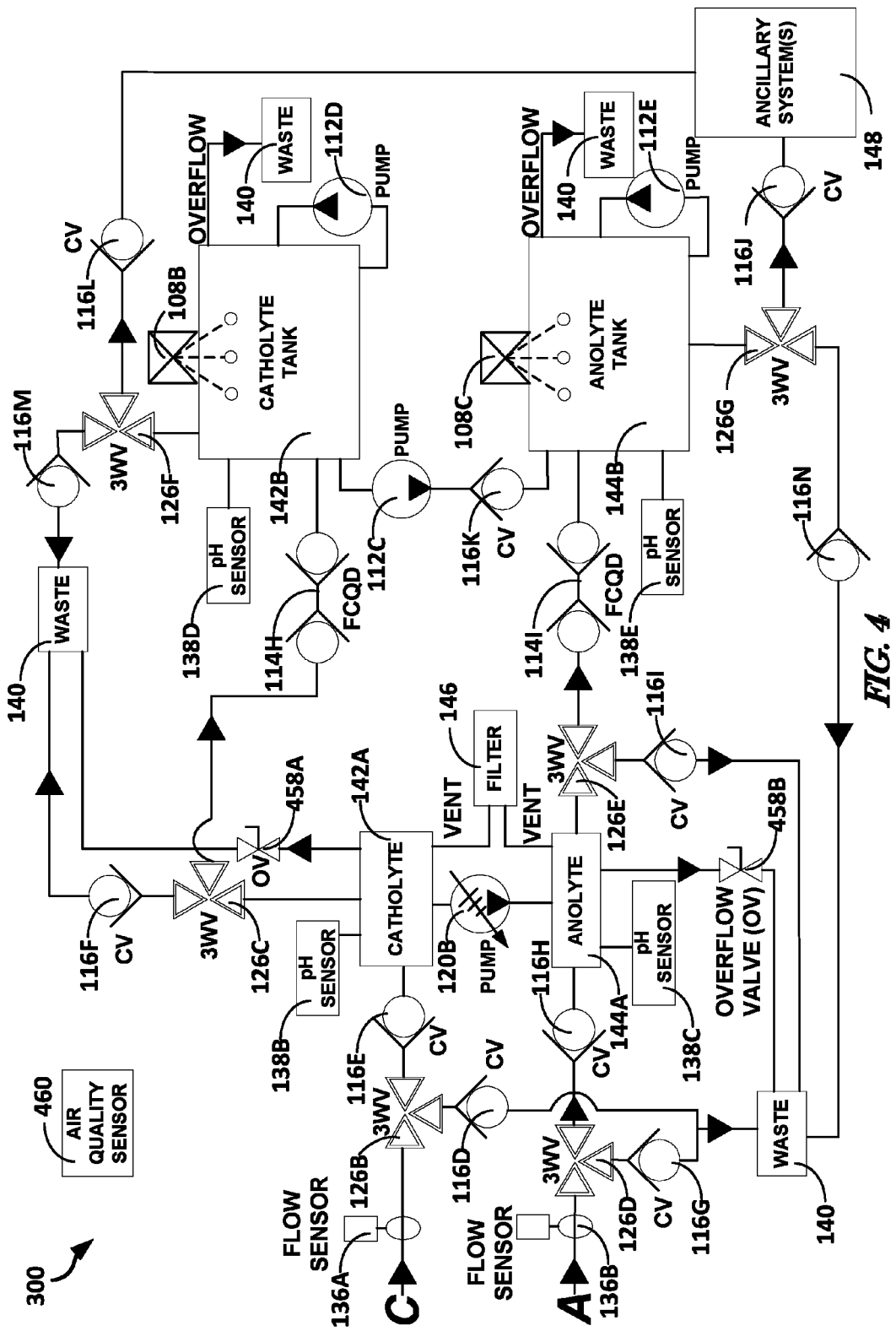
FIG. 4 illustrates, by way of example, a diagram of an embodiment of another portion of the system for production and storage of anolyte and catholyte.

FIG. 3 illustrates, by way of example, a diagram of an embodiment of a portion of another system 300 for production and storage of anolyte and catholyte. FIG. 4 illustrates, by way of example, an embodiment of another portion of the system 300 for production and storage of anolyte and catholyte. While the system (comprising the portion of system 300 and the portion of system 400) is illustrated as including number of check valves (CVs), FCQDs, sensors, flow control devices (variable or static flow control valves), valves (two and three-way valves), and receptacles (e.g., tanks, drains, containers, or the like), it will be apparent that not all items shown are required for an operational system, method, or device suitable for production and/or storage of anolyte and catholyte.

The system 300 including the portions illustrated in FIGS. 3 and 4 is similar to the system 100 including the portions illustrated in FIGS. 1 and 2. The system 300 illustrated in FIGS. 3 and 4, while largely the same as the system 100 illustrated in FIGS. 1 and 2, includes some additional elements as compared to the system 100 illustrated in FIGS. 1 and 2.

The system 300 includes an additional flow control valve 104C situated between the FCQD 114B and the flow control valve 104B. The flow control valve 104C may regulate the flow of fluid from the FCQD 114B. The flow control valve 104B may reduce the flow of fluid from the flow control valve 104C, such as may be based on data from the pressure sensor 122. The remainder of the portion of the system 300 illustrated in FIG. 3, is the same as the portion of the system 100 illustrated in FIG. 1.

The system 300 illustrated in FIG. 4 includes an additional air quality sensor 460, overflow valves 458A-B, check valve 116M, and check valve 116N over the portion of the system 100 illustrated in FIG. 2. The air quality sensor 460 may determine an amount of one or more pollutants in the air around the system (the system of FIGS. 1 and 2 or the system of FIGS. 3 and 4). The air quality sensor 460 may measure one or more of ozone, particulate matter, carbon monoxide, sulfur dioxide, chlorine, and/or nitrous oxide. The air quality sensor 460 may provide data indicating the amount of the pollutant being measured to processing circuitry 456 (see FIG. 7). The air quality sensor 460 may be positioned near the tanks 142A-B and/or 144A-B, such as to monitor an amount of gas being released into the air near the tanks 142A-B and 144A-B.

The overflow valves 458A-B may be used to help ensure that the fluid in the tanks 142A and 144A do not exceed a pre-determined level. The overflow valves may be adjusted (e.g., by the processing circuitry 456 or manually) to alter a flow of fluid therethrough, such as to prohibit or allow water to flow therethrough.

The CV 116M is in fluid communication with fluid from the 3WV 126F. The CV 116M allows fluid from the 3WV 126F to pass therethrough to the waste 140. The CV 116M helps prevent fluid flowing from the waste 140 to the 3WV 126F. The CV 116N is in fluid communication with fluid from the 3WV 126G. The CV 116N allows fluid from the 3WV 126G to pass therethrough to the waste 140. The CV 116N helps prevent fluid flowing from the waste 140 to the 3WV 126G.

Figure 5:
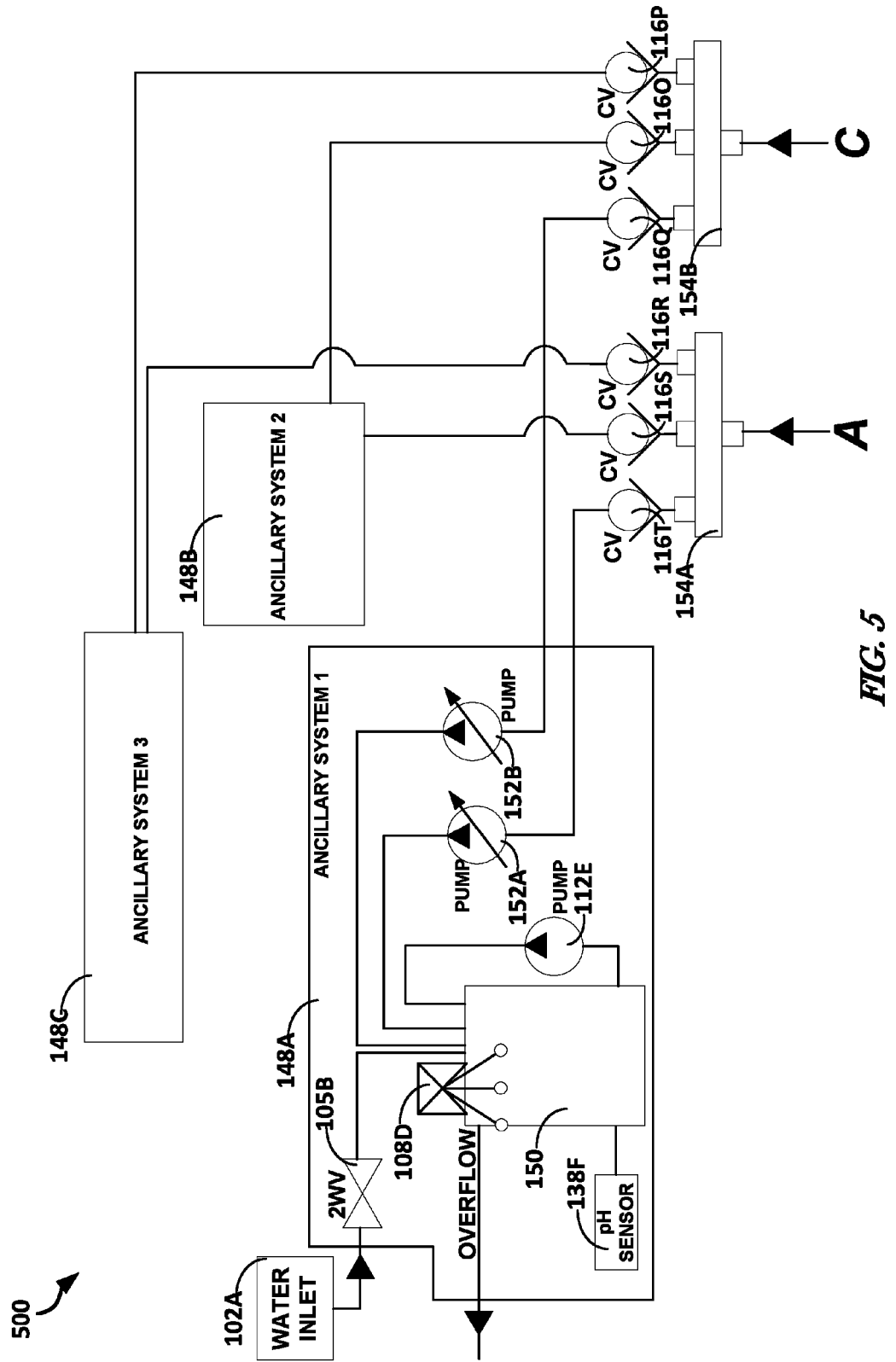
FIG. 5 illustrates, by way of example, a diagram of an embodiment of an ancillary system.

FIG. 5 illustrates, by way of example, a block diagram of an embodiments of a system 500 for connecting systems, such as the systems 100 and 300 illustrated in FIG. 1-4, to multiple ancillary systems 148A, 148B, and 148C. While the system 500 is illustrated as including three ancillary systems 148A-C, any number of ancillary systems, one or greater, may be coupled to the output of the system 100 or 300 using the concepts embodied in the illustrated system 500.

The system 500 as illustrated includes the water inlet 102A in fluid communication with a 2WV 105B. The 2WV 105B, when open, allows water to move from the water inlet 102A to a holding tank 150. The water from the water inlet 102A may be the same or different as water from the water inlet 102 of FIG. 1. The 2WV 105B, when closed, prevents water from flowing to the holding tank 150. The 2WV may be closed if a level sensor 108D indicates that the tank 150 is at or above a threshold liquid level to be detected by the level sensor 108D. The water from the water inlet 102A may be used to dilute the concentration of the anolyte and/or catholyte in the tank 150, such as from the system 100. A circulating pump 112E is in fluid communication with liquid from the tank 150. The pump 112E mixes the fluid in the tank 150.

A pH sensor 138F is in fluid communication with liquid in the tank 150, such as to monitor a pH of the liquid. The pH may be adjusted by increasing or decreasing a flow of the anolyte, catholyte, and/or water to the tank 150.

The system 500 as illustrated includes a variable displacement pump 152A and 152B in fluid communication with respective multi-path flow dividing valves 154A and 154B. A variable displacement pump converts mechanical energy into fluid movement. The amount of fluid moved or a speed at which the fluid is moved may be adjusted while the pump is running, such as to provide more or less anolyte or catholyte to the tank 150.

The flow dividing valve 154A-B performs a similar function as the valve 530 with the valve 154A-B potentially including more paths on which to output liquid provided thereto. The system 500 as illustrated includes a CV 116O, 116P, 116Q, 116R, 116S, and 116T in fluid communication between the valve 154A-B and the ancillary system 148A-C. The flow dividing valves 154A-B are optional in embodiments in which there is only a single ancillary system 148 to supply. The ancillary systems 148B-C are optional as well.

Figure 6:
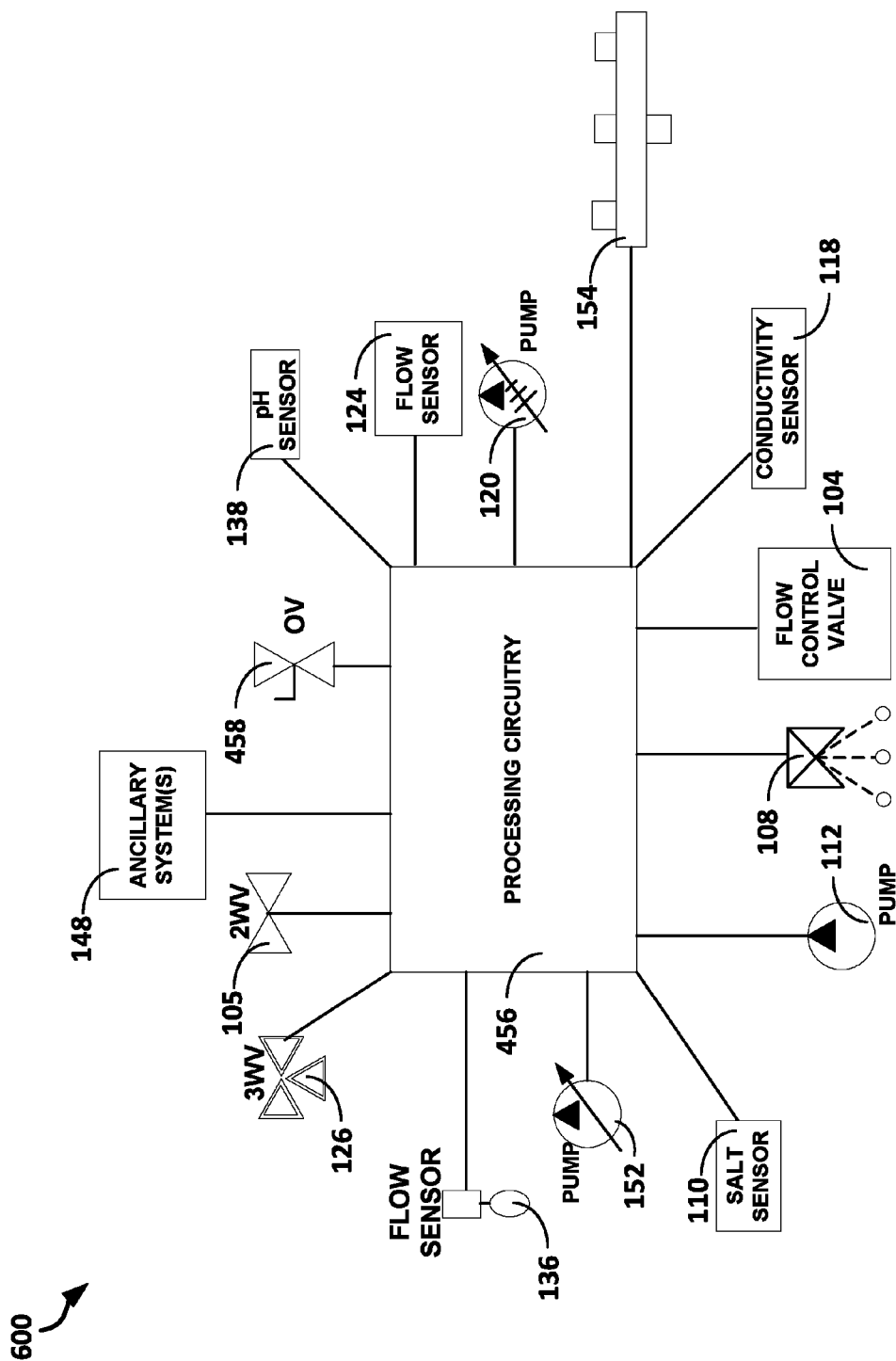
FIG. 6 illustrates, by way of example, a diagram of an embodiment of control circuitry to control one or more items of the system of FIGS. 1, 2, 3, 4, and/or 5.

FIG. 6 illustrates, by way of example, a block diagram of an embodiment of a control system 600 to control items of the system 100, 300, and/or 500. The control system 600 includes processing circuitry 456 electrically coupled, such as by a wired or wireless coupling or connection, to items of the system 100, 300, and/or 500. The processing circuitry 456 includes a hardware processor or other components (e.g., transistor(s), resistor(s), capacitor(s), regulator(s), inductor(s), Boolean logic gate(s), clock(s), multiplexer(s), state logic, memory(s), or the like) configured to receive one or more signal(s) from the item(s) coupled thereto and perform one or more operations in response to the received signal.

The items of FIG. 6 do not include suffix reference designators so as to refer to the item more generically. Thus, for example, the pH sensor 138 refers to one or more of the pH sensors 138A-F. The operations performed by the processing circuitry 456 are performed, such as to automate the operation of the system 100, 300, and/or 500.

The items illustrated as being communicatively coupled to the processing circuitry 456 include a flow control valve, a 2WV 105, a level sensor 108, a salt sensor 110, a fixed displacement pump 112, a dosing pump 120, a flow sensor 124, a 3WV 126, another flow sensor 136, a pH sensor 138, a variable displacement pump 152, a flow dividing valve 154, and an overflow valve 458.

Some operations which the processing circuitry 456 may perform are now described with the understanding that this description is not exhaustive. The processing circuitry 456 may open, close, or change a position of a valve 105, 126, 154, and/or 458 in response to one or more signals received from a sensor 108, 110, 118, 124, 136, and/or 138. The processing circuitry 456 may stop, start, or change a displacement rate of a pump 112, 120, and/or 152 in response to one or more signals received from the sensor 108, 110, 118, 124, 136, and/or 138.

The operations of the processing circuitry 456 may include:

1) decreasing a flow of liquid allowed through the flow control valve 104A or the 2WV 105A, such as by at least partially closing the valve 104A or 105A, such as in response to receiving a signal from the sensor 108A indicating that the tank 106 is sufficiently full.

2) increasing a flow of liquid allowed through the flow control valve 104A or the 2WV 105A, such as by at least partially closing the valve 104A or 105A, such as in response to receiving a signal (or not receiving a signal from the sensor 108A) from the sensor 108A indicating that the tank 106 is not sufficiently full.

3) stopping the pump 112A in response to receiving a signal from the salt sensor 110 that indicates there is a sufficient amount of salt dissolved in the brine in the tank 106.

4) increasing or decreasing a flow of liquid allowed through the flow control valve 104B by at least partially opening or closing the valve 104B, such as in response to receiving a signal from the pressure sensor 122 or a temperature sensor indicating a pressure or temperature of the water moving to the valve 104B, such as to provide a temperature and/or pressure compensated flow control valve.

5) increasing or decreasing a flow of liquid allowed through the flow control valve 104B by at least partially opening or closing the valve 104B, such as in response to receiving a signal from one or more of the flow sensors 124A-B indicating a flow of the water moving to the valve 104B. If it is determined that the flow rate detected by one or more of the sensors 124A-B is too high the flow of liquid through the valve 104B may be reduced. If it is determined that the flow rate detected by one or more of the sensors 124A-B is too low the flow of liquid through the valve 104B may be increased.

6) increasing or decreasing a displacement rate of the dosing pump 120A based on one or more signals received from one or more of the conductivity sensors 118A-B.

7) altering a selected path of the 3WV 126A, 126B, and/or 126D in response to determining it is a specified time or other signal that may trigger the processing circuitry 456 to clean or stop the cleaning of the electrolysis device 132. In one or more embodiments, the pump 112B may be switched on to move vinegar from the tank 128 in response to the path of the 3WV 126A being switched to that path. In one or more embodiments, the 3WV 126B and 126D may be switched to be in the path through the CV 116D and 116G, respectively, in response to the vinegar path of the 3WV 126A being selected. In one or more embodiments, in response to selecting the brine path (the non-vinegar path) the 3WV 126B and 126D are switched to select the path that includes the CV 116E and 116H, respectively.

8) altering a selected path of the 3WV 126C and/or 126E in response to receiving a signal from the pH sensor 138B or 138C, respectively, that indicates that the pH of the catholyte or the anolyte in the tank 142A or 144A, respectively, is (not) within a specific range, which may be stored in a memory of the processing circuitry 456. The selected path may be changed to the path that includes the CV 116F or 116I, respectively, in response to receiving a signal that the pH is not suitable for the catholyte tank 142B or the anolyte tank 144B. The selected path may be changed to the path that includes the FCQD 114H or 114I, respectively, in response to receiving a signal that the pH is suitable for the catholyte tank 142B or the anolyte tank 144B.

9) increasing or decreasing a displacement rate of the dosing pump 120B based on one or more signals received from one or more of the pH sensors 138B-C.

10) altering a selected path of the 3WV 126F and/or 126G or a state of an overflow valve 458 in response to a signal received from the pH sensor 138D or 138E, a level sensor 108B or 108C, or a signal received from the ancillary system(s) 148. The selected path of the 3WV 126F and/or 126G may be switched to the path including the ancillary system 148 in response to receiving a signal indicating to provide catholyte or anolyte, respectively. The selected path of the 3WV 126F and/or 126G may be switched to the path including the waste tank 140, such as in response to receiving a signal from the pH sensor 138D and/or 138E indicating that the pH of the catholyte or anolyte in the tank 142B and 144B, respectively, is (not) within a specified range of pHs. The selected path of the 3WV 126F and/or 126G may be switched to the path including the waste tank 140, such as in response to receiving one or more signals form the level sensor 108B or 108C, respectively, indicating that the level of liquid in the tank 142B or 144B is at or above a level being monitored by the respective sensor 108B or 108C. The overflow valve 458, such as may be situated on the tank 142B and/or 144B may be moved to an open position, such as in response to receiving one or more signals form the level sensor 108B or 108C, respectively, indicating that the level of liquid in the tank 142B or 144B is at or above a level being monitored by the respective sensor 108B or 108C.

11) turning on or off the pump 112C in response to a signal from the pH sensor 138E. The pump 112C may be turned on in response to receiving one or more signals indicating that the pH of the anolyte in the tank 144B is too acidic. The pump 112C may be turned off in response to receiving one or more signals indicating that the pH of the anolyte in the tank 144B is within a specified range of pHs.

12) turning on, off, or changing the rate of displacement of the pump 152A-B in response to a signal received from the pH sensor 138F or the level sensor 108D. The pump 152A-B may be turned on of the displacement rate may be increased in response to receiving one or more signals indicating that the pH of the liquid in the tank 150 is too acidic or too basic, such as by activating or increasing a displacement rate of the pump 152A in response to receiving a signal that indicates the pH is too high or the pump 152B in response to determining the pH is too low. The pump 152A-B may be turned off in response to receiving one or more signals indicating that the level of the liquid in the tank 150 is at or above a level being monitored by the level sensor 108D.

13) opening or closing a 2WV based on a signal received from the level sensor 108D.

Figure 7:
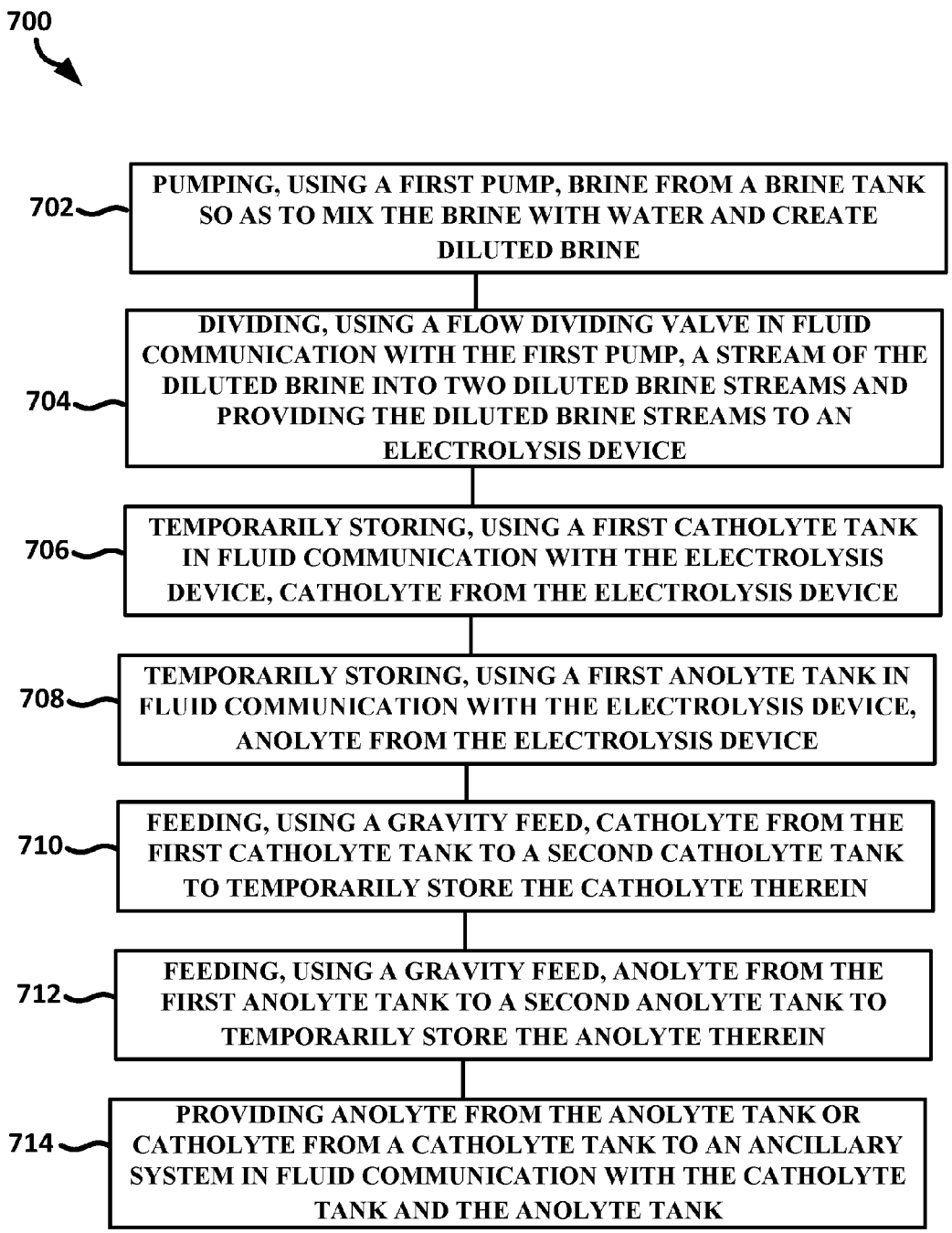
FIG. 7 illustrates, by way of example, a diagram of an embodiment of a method for production and/or storage of catholyte and anolyte.

FIG. 7 illustrates, by way of example, a diagram of an embodiment of a method 700 for production and/or storage of anolyte and/or catholyte. The method 700 as illustrated includes: pumping, using a first pump, brine from a brine tank so as to mix the brine with water and create diluted brine, at operation 702; dividing, using a flow dividing valve in fluid communication with the first pump, a stream of the diluted brine into two diluted brine streams and providing the diluted brine streams to an electrolysis device, at operation 702; temporarily storing, using a first catholyte tank in fluid communication with the electrolysis device, catholyte from the electrolysis device, at operation 704; temporarily storing, using a first anolyte tank in fluid communication with the electrolysis device, anolyte from the electrolysis device, at operation 706; feeding, using a gravity feed, catholyte from the first catholyte tank to a second catholyte tank to temporarily store the catholyte therein, at operation 708; feeding, using a gravity feed, anolyte from the first anolyte tank to a second anolyte tank to temporarily store the anolyte therein, at operation 710; and providing anolyte from the anolyte tank or catholyte from a catholyte tank to an ancillary system in fluid communication with the catholyte tank and the anolyte tank, at operation 712.

The method 700 may further include pumping, using the first pump, the diluted brine solution through a first path of a first three-way valve (3WV) coupled between the first pump and the electrolysis device. The method 700 may further include pumping, using a second pump in fluid communication with a second path of the first three-way valve (3WV), an electrolysis device cleaning solution to the flow dividing valve through the second path of the 3WV.

The method 700 may further include mixing water and salt in a brine tank by including the salt in a first well of the brine tank and water in a second well of the brine tank and adding water to the brine tank, the first well and the second well separated by a dividing wall that is at least partially perforated so as to allow the salt and water to mix to create the brine. The method 700 may further include recirculating, using a pump, brine over the salt in the first well. The method 700 may further include regulating, using a first flow control valve, a flow rate of the water to be mixed with the brine. The method 700 may further include measuring, using one or more flow sensors in fluid communication with the water downstream from the flow control valve, a flow rate of the water, wherein the flow control valve regulates the flow rate of the water based on the measured flow rate.

The method 700 may further include, wherein the first flow control valve is a pressure and temperature compensated flow control valve, and determining, using one or more pressure sensors upstream of the first flow control valve and in fluid communication with the water, a pressure of the water. The method 700 may further include determining, using one or more temperature sensors upstream of the first flow control valve and in fluid communication with the water, a temperature of the water, wherein regulating the flow rate of the water includes regulating based on the determined pressure and temperature.

The method 700 may further include guiding, using a first path of a second 3WV in fluid communication with the catholyte downstream from the electrolysis device and upstream of the first catholyte tank, the electrolysis cleaning solution to a waste tank. The method 700 may further include guiding, using a second path of the second 3WV, the catholyte from the electrolysis device to a catholyte tank. The method 700 may further include guiding, using a first path of a third 3WV in fluid communication with the anolyte downstream from the electrolysis device and upstream of the first anolyte tank, the electrolysis cleaning solution to a waste tank. The method 700 may further include guiding, using a second path of the third 3WV, the anolyte from the electrolysis device to an anolyte tank.

Systems and Methods for Cleaning and Sanitizing Surfaces

It would be advantageous to identify a method for de-soiling and/or decontaminating environmental contact surfaces to a degree of cleanliness that the application of an approved sanitizer or disinfectant may reduce target pathogens below their infective dose. It may be beneficial if the cleaner(s) used to decontaminate the surface were not antagonistic with the sanitizer(s) that are used after decontamination. It may also be beneficial if the cleaner(s) and sanitizer(s) did not leave an alkaline film residue behind after the diluent water evaporates. Alkaline residues promote colonization of biofilms by providing the basic surface film foundation upon which they adhere and find suitable habitat. Also, when alkaline residues from floor cleaning detergents are rewetted, there is a reduction of the coefficient of friction causing the floor to become slippery leading to slip/fall risks.

Embodiments discussed relate to cleaning and decontaminating (i.e. sanitizing) hard and/or soft contact surfaces as well as biological surfaces, such as skin, tissues, hides, hoofs and hands. In one or more embodiments, a catholyte solution serves as the cleaning agent and an anolyte solution serves as the sanitizing agent. Catholyte is an amphoteric surfactant and has a reduced surface tension as compared to distilled water. With its relatively high pH and reduced surface tension, catholyte has properties for interrupting the interfacial bond between contaminants and a surface. In one or more embodiments, a process control creation and/or validation process may be used to determine properties of the surface contaminants and to establish a protocol for the application of catholyte solutions to clean a surface. By using a hand held adenosine triphosphate (ATP) luminometer, the relative effectiveness of a cleaning protocol (e.g., each step in a cleaning protocol) may be measured.

Some entities use toxic chemical concentrates that they then dilute on site around a time of use for cleaning and sanitization of their facilities and/or equipment. These toxic chemicals may be detrimental to foodservice and other retailers as the toxic chemicals may get into the food or drinks that are served or patrons and employees of the facilities may otherwise come into contact with the toxic chemicals. Handling of these toxic chemical concentrates poses a risk to employees giving rise to the need for personal protective equipment (PPE) eye and body wash stations as required by OSHA regulations. Also, the packaging of the chemicals includes toxins thereon, providing an additional environmental impact.

Anolyte and catholyte may be generated on site, on demand, and may be used in tandem in place of these packaged toxic chemical concentrates. Anolyte and catholyte products may be generated in an Electrochemical Activation (ECA) process. This makes anolyte and catholyte production and use a cost-effective solution for the sanitization and cleaning needs of a facility.

For decades companies that make toxic chemical concentrates have been selling the convenience of their so-called "one-step cleaner/sanitizers". Some businesses, however, are increasingly aware that these single step procedures are not effective enough and the chemicals that they use for these processes are every bit as toxic as many years ago. Because the measure of "clean" has historically been a subjective, visual observation, todays "accepted" industry norms is to only measure and quantify the sanitizing step, as if every surface has a uniform degree of contamination on it. For example, a difference between a sanitizer and a disinfectant is that the test method used to validate efficacy of disinfectants adds a bioburden to the assay, whereas sanitizer test methods do not include a bioburden challenge. This concept then, of quantifying "clean" with accurate ATP measure is new to everyone and is disruptive both in thought and in practice.

The United States Environmental Protection Agency (EPA) interprets and enforces the Federal Insecticide Fungicide and Rodenticide Act (FIFRA). FIFRA establishes maximum contamination levels (MCLs) for each approved sanitizer, disinfectant, insecticide, and so forth. These sanitizers, disinfectants, and insecticides are collectively referred to as "pesticides". The purpose of FIFRA is "to regulate the marketing of 'economic poisons' and other devices". Congress calls these chemical compounds "economic poisons". This title is due to the long term adverse health effects associated with the production, packaging, distribution, sale and ultimate discharge of the solutions into the environment. Empty chemical concentrate packages inevitably wind up in landfills, where residues of their toxic content eventually leech into the ground and ultimately return to us in our water, air, and food stuffs.

While effective sanitizing may be quantified by a certain reduction of microorganisms, cleaning has had no equivalent measure. When employees at the Food and Drug Association (FDA) Center for Food Safety and Applied Nutrition (CFSAN), United States Department of Agriculture (USDA) Food Safety and Inspection Service (FSIS), or Center for Disease Control and Prevention (CDC) Viral Special Pathogens Branch (VSPB) are asked to describe or define "clean", their official response is "clean to sight and touch". No quantitative measure is provided.

Without a quantitative measure and the establishment of threshold limit value (TLV) for surface contaminations, bioburdens (biofilms) may overwhelm an approved sanitizer and/or disinfectant. It is not possible to sanitize or disinfect filth. Rather, filth must be removed before any approved sanitizer or disinfectant may reasonably be expected to effectively disinfect or sanitize.

Even though it is well known that colorimetric test strips for measuring a chemicals titer (concentration) are inaccurate, regulations allow their use to verify the concentration of sanitizers and disinfectants used for either food contact surfaces, or general environmental disinfection. This policy ignores the fact that in chlorine based systems, free available chlorine (FAC) is comprised of two parts. One is hypochlorus acid (HOCl) and the other is hypochlorite ion (OCl$^-$). HOCl is a powerful, broad-spectrum biocide whereas OCl– is a very weak, at best. The proportion of each is determined entirely by its pH, yet pH is not a required measure for regulatory compliance. Other disconnects between compliance and a reasonable standard of care include the failure of regulations to consider source water chemistry for the diluent. Little if any attention is paid to source water for the diluted product, yet water accounts for the overwhelming mass of any sanitizer or cleaner prepared from concentrates. Over 80% of packaged chemical concentrates have a dilution ratio of greater than one hundred to one (100:1) (water to cleaner/sanitizer/disinfectant ratio). The most that is said about the diluent in manufacturers label instruction, in only some instances, is that total hardness or total dissolved solids (TDS) should not exceed some amount, such as 400 parts per million (ppm). In general, one (1) grain of hardness is equal to 17.1 ppm TDS (e.g., 400 ppm TDS is about equal to 23 grains of hardness). In summary, current accepted protocols and regulations sacrifice efficacy for convenience and suffer from an abject failure to integrate cleaning measurement technology (e.g., ATP luminometers) into their process requirements.

One or more embodiments discussed are rooted in the concept that we may improve that which we measure. A bioluminescence of luciferase may be used as a fast and highly accurate way to economically and quantitatively measure or otherwise quantify "CLEAN".

ATP is a common energy "packet" used by cells and its presence is evidence that a living or destroyed cell is on the surface. All cells comprise organic "bioburdens" as they consume the antimicrobial chemical and physical characteristics of all sanitizers and disinfectants. Though science and technology have advanced rapidly at an ever-increasing rate, our regulations regarding cleaning and sanitizing have remained artifacts from an era before measurement tools such as ATP luminometers.

A cleaning process may be validated using ATP test methods, such as by measuring surface contamination before and or after a cleaning process. A comparison of measurements may be used to enable the establishment of a cleaning protocol (e.g., an optimized cleaning regime). The sequential, pre-ordinal process of cleaning before sanitizing may include specific sequential steps using non-traditional ECA cleaning and sanitizing agents generated by the application of energy to water and a melted (dissolved) salt through a membrane type ECA cell.

Each type of contact surface (which may be dependent on the use of the contact surface) may have a unique treatment process developed using a clinical three batch validation process using ATP luminometers to measure whatever bioburden may be remaining on the surface after each specified cleaning step. Cleaning and sanitizing steps may include a description of cleaning tools such as buckets, towels, brushes and squeegees, time, solutions application or dispersal, and recommended final ATP TLV's. Also, in one or more embodiments, kinetic factors including temperature and friction form flow and pressure at specific volumes and/or time may be included in the protocol. This protocol may then be recorded and may become a protocol for the facilities Evolved Sanitary Operations Platform (ESOP) which may include separate cleaning and sanitizing standardized Operating Procedures (SOPs) for each unique surface and/or application in the facility.

Figure 8:
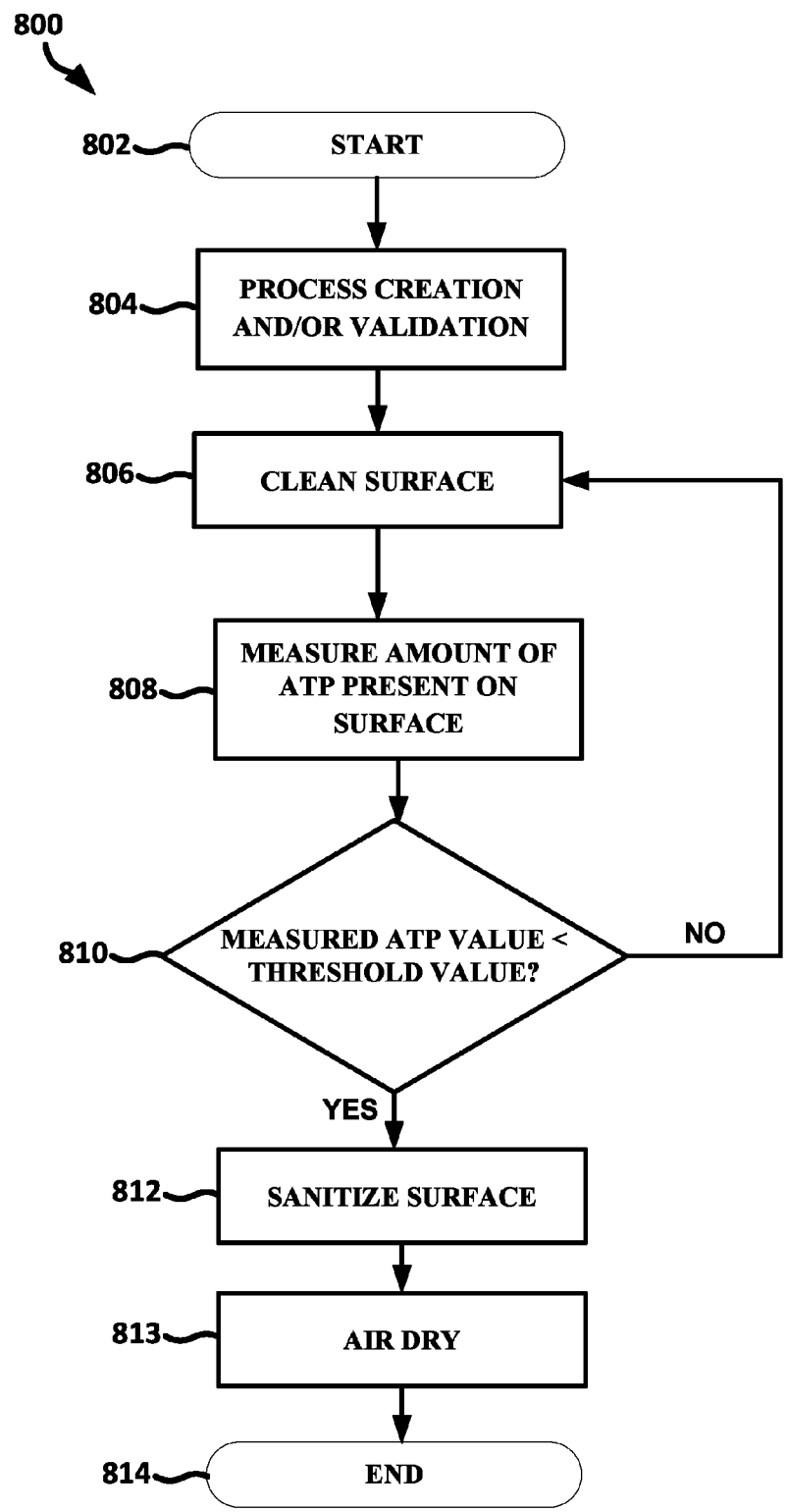
FIG. 8 illustrates, by way of example, and embodiment of a method for cleaning and sanitizing a surface.

FIG. 8 illustrates, by way of example, a flow diagram of an embodiment of a method 800 for cleaning and sanitizing a surface. The method 800 as illustrated includes: starting at operation 802; optionally creating and/or validating a cleaning process at operation 804; measuring an amount of ATP present on the contact surface at operation 806; determining if the measured amount of ATP is less than (or equal to) a threshold value at operation 808; cleaning the contact surface at operation 810; in response to determining the measured amount of ATP is less than (or equal to) the threshold value the surface may be sanitized at operation 812; returning to operation 810 in response to determining the measured amount of ATP is greater than the threshold value; air drying the contact surface at operation 813, and the method 800 ends at operation 814. It is noted that beyond clean out of place (COP) procedures, the same methodology may be applied to clean (and sanitize) in place (CIP, or CSIP) processes as are common in food and beverage processing along with certain retail food applications including ice makers and remote dispensing freezers commonly used for dairy products and yogurts.

Common surfaces requiring cleaning and sanitization include food and beverage contact surfaces, hand railings, chair arms and frames, faucets and handles, elevator push buttons, menus, door push plates, pull handles and levers, upholstery fabrics including leathers, tiles, glass, polymers, linens, fabrics including carpeting, hard contact surfaces such as stainless steel, floors, walls and ceilings along with fixtures and equipment, wares, utensils, implements, keyboards, push buttons, laminates, stone and myriad of other environmental contact surfaces. Other surfaces for such an application is the surfaces of higher life forms whether mammalian and/or other endothermic vertebrates.

The method 800 may include producing the catholyte and/or anolyte, such as by using a portion of the system 100 or 300 illustrated in FIGS. 1-4. The catholyte may be produced as a product of a dilute salt-water electrolysis process. The salt-water electrolysis process may be performed using sufficiently pure water (e.g., less than one part per million (ppm) of each of hardness, fluoride, iron, magnesium, and borax and borate). The water may be diluted with high purity culinary salt to create brine of a specific salt concentration and/or conductivity. The brine may then be processed through a dielectric membrane type electrolysis device that takes the brine as input and produces catholyte and anolyte as output. The catholyte (cleaning) and anolyte (sanitizing) solutions generated from such a process have a character determined in part by the purity of the ingredients used and the continuous accurate control of process variables (flow rate, electrical conductivity and electrical current) yielding highly effective and reasonably stable cleaners and sanitizers. The catholyte and anolyte may be used as produced by the electrolysis device or may be diluted with other chemicals, such as water, anolyte, or catholyte to modify the pH and/or concentration of the anolyte or catholyte to a specified level.

The operation 804 may include determining the threshold value and/or providing steps to be performed in carrying out a cleaning and/or sanitizing process. Each specific cleaning and treatment (sanitizing and/or disinfectant) process may undergo a process validation at operation 804 that may be similar to a clinical approach to process validation. A corrective action for a surface found to be not clean during process validation may be re-clean (according to a protocol). The additional time, kinetics, and solutions involved in finally achieving clean may be taken into account for the next process validation test. Once a process is found to be effective, the process may be repeated a number of times. When a specified number of consecutive process validation tests are accomplished, the mean of their results may be used to establish specific step by step cleaning protocols for the process. A terminal sanitizing process may then be established, such as may identify the anolyte titer, pH, method of application, and contact time. Temperature may or may not be considered in the sanitizing process, as anolyte of a given efficacious titer does not lose its antimicrobial properties whether it is in solid form as ice, a boiling liquid, or as steam or condensate from steam, aerosol, a gel or a foam.

Where many if not all existing cleaning protocols for general environmental disinfection whether domestically, in health care, in market verticals such as the cruise industry, lodging, food service or retail food applications use only subjective measures of clean such as clean to "sight and touch", this process may include using a quantitative process validation using ATP luminometers to determine whether a surface is clean enough to be sanitized, such as at operation 806.

The threshold limit value (TLV) may be determined based on one or more properties of the contact surface and/or an intended use of the contact surface. For example, a pipe or wall in a warehouse may have a higher threshold value of ATP than a table at a restaurant because of the intended uses of the contact surfaces. In another example, a porous or permeable table made of a material that biofilms readily grow on may have lower threshold value than a table made of material that biofilms do not readily grow on. This may be because once biofilms start building on the permeable or porous surface, the biofilms may spread to harder to reach/clean areas and grows relatively easier than on the other surface.

Determining the TLV may include using the process control creation and/or validation process to identity a threshold value to help prevent microbial and other hazards. Such a process may be included in a Hazard Analysis Critical Control Point program and in the development of its prerequisite program for standard sanitary operating procedures (SSOP's). The ATP TLV may become a critical control point (CCP) in the overall cleaning and/or sanitizing process (es).

Identifying critical control points (critical control point (CCP) is a point, step, or procedure in a risk control program where a preventative control may be applied reducing risk to an acceptable level of protection (ALOP). Examples: fire is a physical hazard, as are slippery floors. Chemical burns to a person, and/or chemical adulterations in foods are chemical hazards. Microbial growth of pathogens in potentially hazardous foods and/or cross contamination and resulting disease transmission are reasonably controlled by establishing critical limits for each CCP (a critical limit is the maximum or minimum values to which a physical, biological, or chemical hazard must be controlled at a CCP to ensure an acceptable level of protection (ALOP)); establishing CCP monitoring requirements (monitoring activities are necessary to ensure that the ESOP processes are consistently controlled at each CCP; each monitoring and measurement procedure and its frequency may be listed in each ESOP); establishing corrective actions (for each CCP failure, a specific predefined corrective action, and re-measurement must be made. CCP failure incidents along with preplanned corrective actions may be mandatory requirements in each ESOP); establishing record keeping procedures (logs of all adverse CCP incidents including time, date, location, personnel, consequence, corrective actions along beginning and ending measurements and photos/videos, recordings as appropriate); establishing procedures for verifying the HACCP system is working as intended.

Validation of a process ensures that the plans do what they were designed to do; that is, they are successful in ensuring continuous ALOPs. Process validation is quantitative and follows clinical method and good laboratory practices (GLPs) as may be appropriate for certain preventative risk controls. A process authority and/or a certified industrial hygienist along with a recognized laboratory using internationally recognized test standards typically perform process validation. The verification may help ensure the plan is adequate and is working as intended. Verification procedures may include such activities manual temperature verifications and/or pH measurements, or as review of the overall ESOP or specific CCP records, critical limits and microbial and/or ATP sampling and analysis.

The operation at 806 may include using an ATP luminometer to determine the amount of ATP on the contact surface. ATP is a molecule produced by living cells. An amount of ATP present on a surface gives a direct measure of the amount of biological entities on the contact surface. ATP may be quantified by providing luciferase to the surface and then measuring an amount of light produced in reaction to the luciferase. The amount of light is directly proportional to the amount of biological energy present on the contact surface. ATP luminometers quantify the maximum ATP TLV for bioburdens on a clean surface.

The operation at 808 may include first determining the threshold value, such as by performing the optional step 804.

Cleaning the surface (e.g., operation 810) may include using a catholyte solution. The catholyte solution may have a specific pH depending on characteristics (e.g., hardness, permeability, chemical makeup, etc.) of the contact surface to be cleaned. The chemical makeup of the contact surface may indicate how susceptible the surface is to biofilm buildup. The permeability may indicate responsive the surface will be to the cleaning process. The surface hardness and smoothness may also indicate how susceptible the contact surface is to biofilm buildup.

The catholyte solution may include an emulsifier added thereto or used separately to clean the surface. The catholyte may be used in conjunction with kinetics in the form of heat, friction, turbulence, pressure and flow. That is, cleaning of the contact surface may include treating the surface with catholyte solution with or without an emulsifier or added kinetics, treating the surface with catholyte with or without added kinetics and then treating with an emulsifier, or the emulsifier may be applied before the surface is treated with the catholyte solution with or without added kinetics. The emulsifier may help bind oil to water and remove biofilm that might remain without the emulsifier.

One or more forms of kinetics may be used to help allow for the interruption of the interfacial bond between substrate and contaminant. Reduced surface tension along with significant physical activity (scrubbing and/or temperature change) may be combined with cationic reactions and the production of hydroxyls to work together to interrupt the interfacial bond between the surface material and foreign contaminants. The kinetic agent may be used before, during, or after, treatment with the catholyte. The kinetic agent may include a process or product to help speed up or increase the effectiveness of the treatment with the catholyte. Example kinetic agents may include friction, such as a user scrubbing with the catholyte, and/or introducing a temperature difference between the catholyte and the contact surface, such as by heating or cooling the contact surface or catholyte.

Catholyte is an amphoteric surfactant, a cleaner with reduced surface tension and an elevated pH. The catholyte solution produced, in one or more embodiments, may have pH greater than seven (7). In one or more embodiments, the catholyte may have a pH in a range of about 10.3 and about 13.5.

Operation 812 may include sanitizing the surface. Sanitizing the contact surface may be performed after it is determined that the level of ATP present on the surface is below the threshold value, at operation 808. The operation 812 may include using an anolyte on the contact surface. The anolyte may be created using an ECA process, such as is described previously with regard to the catholyte. The anolyte may be of a specified concentration. The anolyte may include a specified pH. The anolyte may include a specified titer. The operation 812 may include using one or more treatment steps to effectively sanitize and/or disinfect the surface. Treatment steps may include a description of cleaning tools such as buckets, towels, brushes and squeegees, contact time, solutions application and/or dispersal, such as is discussed in more detail herein.

Anolyte is predominantly comprised of HOCl when its pH is above 6.0. Anolyte is a broad spectrum sanitizer and disinfectant. Both catholyte and anolyte are metastabilised solutions in dynamic equilibrium. The stability of these solutions, insofar as their ability to maintain a specific FAC (free available chlorine) concentration or pH, is directly related to the design of the electrolytic cell, its materials and catalytic surfaces and the attention to the combustion physics that drive their creation in an ECA process. The method 800 ends at operation 814 after the sanitization step is complete.

Example applications of embodiments of the method 800 may include: biofilm control in water features that in turn prevent amoeba survival reducing risk of *Legionella*, hot and ambient potable water systems; dental unit water line protection, norovirus control; food contact surface sanitizers; swimming pools and spas; showers and locker rooms; floor cleaning, and automated floor cleaning equipment; carpet cleaning and deodorization; mold remediation; fungal controls; catholyte made and diluted with DI water may be an effective glass cleaner; infectious disease controls, both surface decontamination and inactivation; cleaning and decontamination applications; catholyte may replace the use of dish detergents in ANSI NSF Std 3 listed mechanical ware washing equipment and anolyte may be used as the chemical sanitizer, the two may also replace most high volume chemicals used in commercial laundry; decontaminate and disinfect personal protective equipment (PPE), personnel, and equipment; ice machines, dosed to prevent organic growth on harvest plates and in sumps; ready to eat fruit and produce decontamination and surface sanitization in the garden manger for a very efficacious process of surface decontamination and disinfection of fruit or other produce or foods; ultrasonic fogging for extensive extension of shelf life of living plants including perishable fresh fruit and produce, preserving freshness, hydration, turgidity and nutritional components; hand and body hygiene systems and applications; wound care; a variety of therapeutic applications.

Systems and Methods Including Conduit Manifold and (Nested and/or Flow Reversible) Loops One or more embodiments relate to providing fluid (e.g., liquid, gas, or other flowable material) flow in multiple directions in the same conduit. One or more embodiments relate to including nested flow loops, which may each supply fluid. One or more embodiments relate to including nested loops on multiple floors of a building.

Reversing the flow of the fluid may help in removing bacteria, biofilm, virus, rust, oxidation, or other undesirable entity or item in the conduit, such as to help clean and/or sanitize the conduit. A reversible flow may change pressure dynamics at extreme ends of the distribution loop providing better steady pressure state flow controls as compared to other systems.

Figure 9:
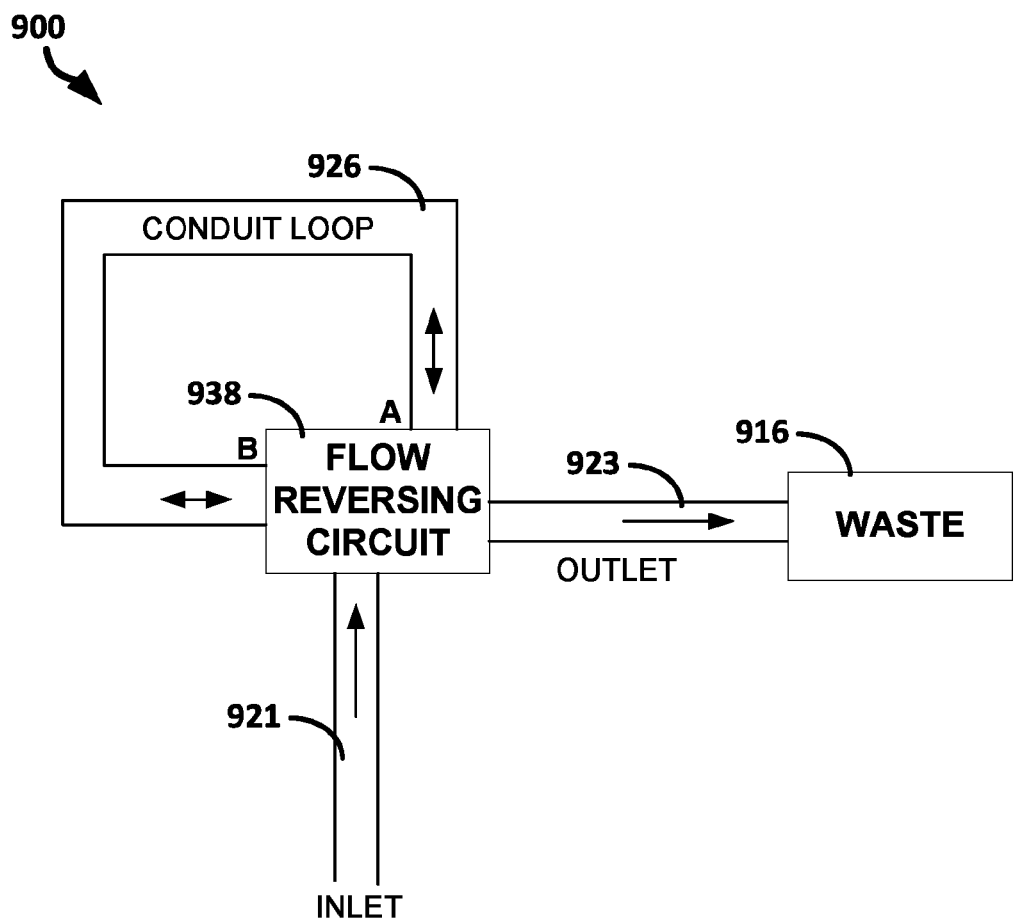
FIG. 9 illustrates, by way of example, a diagram of an embodiment of a circuit loop conduit system in which a fluid flow therethrough can be reversed.

FIG. 9 illustrates, by way of example, a diagram of an embodiment of a system 900 that includes a reversible recirculating flow of fluid in a conduit. The system 900 as illustrated includes an inlet 921, a flow reversing circuit 938, a conduit loop 926, an outlet 923, and a waste receptacle 916.

The inlet 921 provides a fluid (e.g., water, cleaner, sanitizer, other fluid, or a combination thereof) to the flow reversing loop 938. The flow reversing loop 938 includes components, such as valves, switches, conduits, or other items, or a combination thereof that provide fluid paths for fluid to flow to the conduit loop 926. The fluid paths include a first fluid path that provides fluid to the conduit loop at "A". A second fluid path that provides fluid to the conduit loop at "B". When fluid flows through the first fluid path, the fluid flows from "A" to "B", back through the flow reversing loop 938, to the outlet 923, and then to the waste receptacle 916. When fluid flows through the second fluid path, the fluid flows through the conduit loop 926 from "B" to "A", back through the flow reversing loop 938, to the outlet 923, and to the waste receptacle 916.

Since the fluid can flow through the same conduit loop 926 in two directions, the flow reversing circuit 938 can reverse the flow of the fluid. Such fluid flow reversal can help in removing biofilm or other buildup on a surface (an internal surface) of the conduit loop 926.

Figure 10:
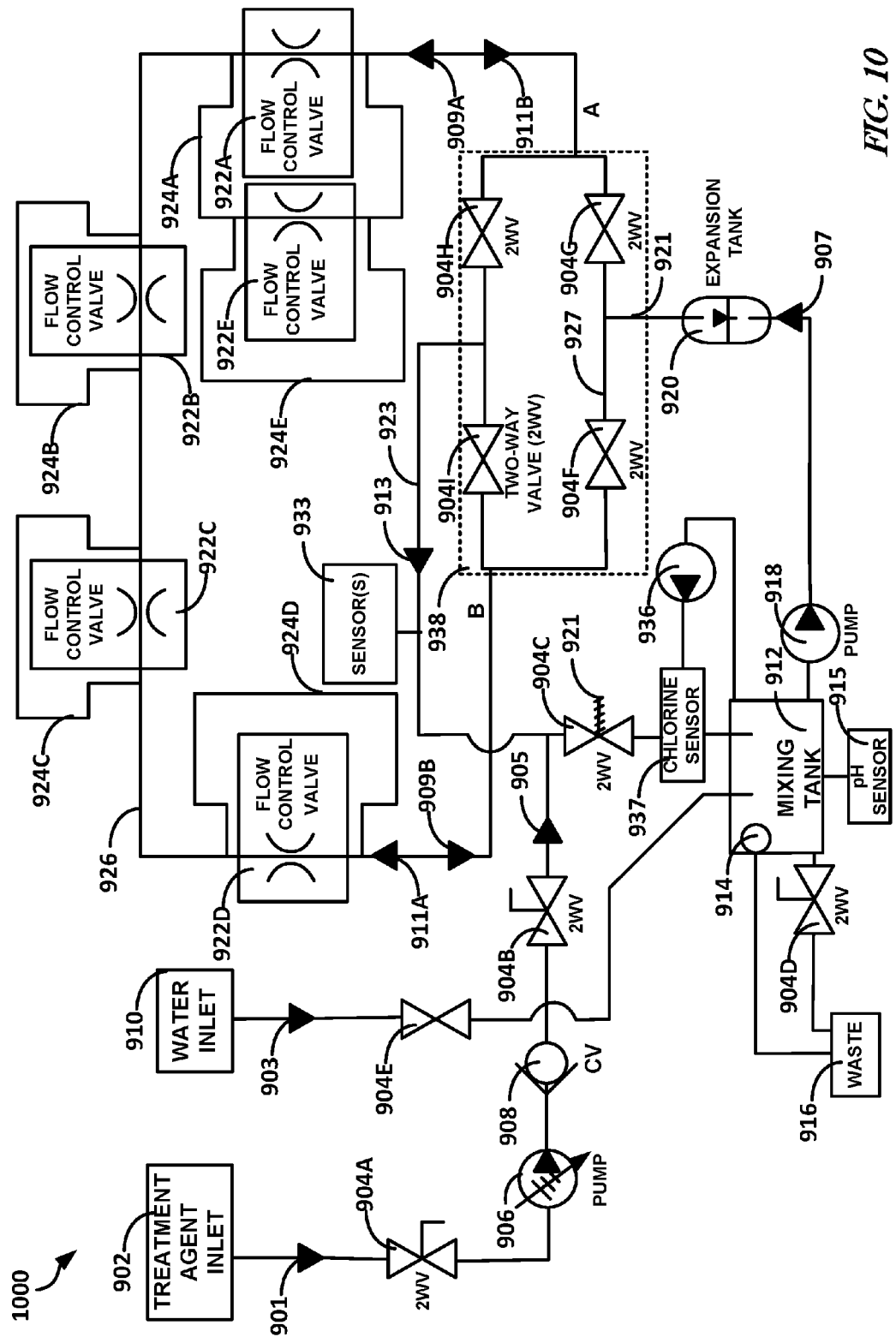
FIG. 10 illustrates, by way of example, a diagram of an embodiment of a circuit loop conduit system to provide a continuous flow of fluid(s).

FIG. 10 illustrates, by way of example, a diagram of an embodiment of a system 1000 that includes a reversible recirculating flow of fluid in a conduit. The system includes a nested circuit loop 938 where flow directions are determined by the opened or closed position of four (4) 2WV's in the nested circuit loop 938. The flow rate of fluid in the nested circuit loop 938 may be determined by a degree of closure of 2WV 904C. The degree of closure of the 2WV 904C may be determined by pressure against a pressure sensor (sensor(s) 933) upstream of 2WV 904C.

While the system 1000 is illustrated as including a number of check valves (CV), sensors, flow control valves, two-way valves (2WV), receptacles (e.g., tanks, drains, containers, or the like), pumps, and inlets, it will be apparent that not all items shown are required for an operational system, method, or device suitable for reversing the flow of a fluid in a conduit. The lines connecting numbered items are conduits. The junctions between conduits may include splitters and/or valves, for example.

The system 1000 as illustrated includes a treatment agent inlet 902. A treatment agent from the treatment agent inlet 902 may be in fluid communication (i.e. through a conduit) with a two-way valve 904A in the direction indicated by arrow 901. The treatment agent from the treatment agent inlet 902, in one or more embodiments, includes anolyte. A 2WV may be any device that, when open, allows fluid to flow in either direction and, when closed, stops fluid from flowing through the device. In some embodiments, a two-way valve may be a solenoid valve and may be either "on" or "off" (open or closed), such as to allow fluid flow or block fluid flow, respectively.

The 2WV 904A may be in fluid communication with a dosing pump 906. A dosing pump may be a device that moves fluid with a controllable discharge rate. The dosing pump 906 may be used to provide sanitizer from the sanitizer inlet 902 to a tank (e.g., tank 912). A dosing pump may be coupled to controller (e.g., processing circuitry 456, see FIG. 11) which enables the fluid flow from the pump to be monitored and adjusted (e.g., automatically, which means without human interference after deployment). "Fluid communication" as used herein may include items being connected by a conduit (e.g., a tube, pipe, or the like) that is capable of carrying fluid from one item to another item in fluid communication therewith.

The dosing pump 906 may be in fluid communication with a check valve 908. A check valve may be a one-way valve that allows fluid flow in only one direction. The check valve 908 allows the sanitizer from the pump 906 to flow through to 2WV 904B. The CV 908 prevents fluid from flowing from the 2WV 904B to the pump 906. The 2WV 904B may be a manual shut off valve to isolate the treating agent provisioning system from the rest of the system.

The 2WV 904B either allows or prohibits fluid from the check valve 908 to flow to in the direction of arrow 905 to a union with recirculated fluids flowing in the direction of arrow 913 and to 2WV 904C.

The 2WV 904C includes a variable nozzle 921 that allows a flow rate of fluid through the 2WV 904C to be adjusted based upon pressure as determined from the sensor(s) 933. Such adjustment provides a measure of control for fluid flow rate and/or pressure in a conduit loop and/or a flow reversing loop. The 2WV 904C provides fluid, such as sanitizer or fluid from a flow reversing loop, to the mixing tank 912.

The mixing tank 912 may be a mixing container capable of holding the sanitizer and/or water. The material from which the tank is formed may be one that does not interact with the sanitizer, the water, or fluid from the conduit loop or flow reversing loop.

The mixing tank 912 may include a level monitor 914. The level monitor 914 monitors a height of fluid in the mixing tank 912. The level monitor 914 may provide one or more signals indicative of the height of the fluid in the tank 912 to the controller (e.g., the processing circuitry 456 and/or one or more motors or other actuators electrically coupled to the processing circuitry 456). The controller may open a 2WV 904D to purge, to a waste receptacle 916, fluid from the tank 912 in response to determining a height of the fluid is greater than a threshold height. The 2WV 904D provides excess fluid in the tank 912 to a waste receptacle 916 (e.g., a drain, a tank, or the like) and/or open of close 2WV 904E to add water, such as to help maintain a set point level.

The system 1000 as illustrated includes a water inlet 910. Water from the water inlet 910 may be in fluid communication with a 2WV 904E in the direction indicated by arrow 903. The 2WV 904E either allows water to flow or prohibits water from flowing from the water inlet 910 to the tank 912. The level monitor 914, in one or more embodiments, may be an open overflow conduit used as back-up control for maximum fluid levels in the mixing tank 912.

The water from the water inlet 910, in one or more embodiments, may be filtered, softened, and/or reverse osmosis water (permeate). In one or more embodiments, the water from the water inlet 910 includes less than one part per million (ppm) of each of hardness, fluoride, iron, magnesium, and borax and borate.

A pH sensor 915 may be in fluid communication with fluid in the tank 912. The pH sensor 115 monitors pH of fluid in the take. The pH sensor 915 may provide a signal to the controller indicative of the pH of the fluid in the tank 912. The controller may adjust whether water flows from the water inlet 910 to the tank 912 by opening or closing the 2WV 904E. The controller may adjust whether (and how much) sanitizer flows to the tank 912 by opening or closing the 2WV 904A, 904B, and/or 904C, and/or adjusting the nozzle 921 or a flow of fluid provided by the dosing pump 906.

A pump 918 may cause fluid in the tank 912 to flow towards an expansion tank 920, in the direction of arrow 907. The pump 918 may be made operable or inoperable using a signal from the controller. An expansion tank protects closed fluid systems from excessive pressure fluctuations. An expansion tank may include an air filled bladder therein to absorb excess water pressure fluctuations, such as may be caused by thermal expansion, water hammer, excess flow, pump dynamics and/or other factors.

The expansion tank 920 provides fluid from the pump to a flow reversing loop. The flow reversing loop illustrated in FIG. 9 includes four 2WVs (2WV 904F, 2WV 904G, 2WV 904H, and 2WV 904I). Each of the 2WVs 904F-I may be controlled by the controller. The controller may open and close each of the 2WVs 904F-I independently.

When the 2WVs 904F and 904H are open and the 2WVs 904G and 904I are closed, fluid from the pump 918 and/or expansion tank 920 travels through the 2WV 904F and may be prohibited from flowing through the 904G and 904I. The fluid then flows to a conduit loop 926, such that the fluid flows in the direction indicated by arrows 911A and 911B, through the 2WV 904H, to the 2WV 904C in the direction of arrow 913, and to the tank 912.

When the 2WVs 904G and 904I are open and the 2WVs 904F and 904H are closed, fluid from the pump 918 and/or expansion tank 920 travels through the 2WV 904G and may be prohibited from flowing through the 904F and 904H. The fluid then flows to the conduit loop 926, such that the fluid flows in the direction indicated by arrows 909A and 909B, through the 2WV 904I, to the 2WV 904C in the direction of arrow 913, and to the tank 912. Alternatively, such as in extreme fluid demand situations, all reversible loop 2WV's (e.g., 904F-I) may be open simultaneously, such as to enable maximum flow and pressure throughout the entire system 1000. By switching which pair of 2WVs of the flow reversing loop are open and which pair of 2WVs of the flow reversing loop are closed, the controller may reverse the direction of fluid in the conduit loop 926. Such reversal of fluid flow may help remove biofilm from the conduit loop 926. Biofilms may grow and form to withstand fluid flow in one direction and may remain vulnerable to fluid flow in an opposing direction. The ability to expose the biofilms to fluid in the opposing direction may help remove the biofilm. By exposing the biofilm to a proper fluid, such as a sanitizer, and flow kinetics, the fluid may help remove biofilm in conduit loop 926 and inactivate or destroy microorganisms that seek harborage within the biofilm matrix. A continuous flow throughout the conduit loop 926 ensures biofilms may not reform, attach, and/or propagate.

The conduit loop 926 may include one or more conduit sub-loops 924A, 924B, 924C, and/or 924D. The conduit sub-loops 924A-D may provide fluid flow to an extremity of a water line, for example. Consider a main water line of a house. The conduit loop 926 may be the main water line and the conduit sub-loops 924A-D may be, for example, a line coming off the main line to a bathroom, kitchen, utility sink, laundry room, spigot, or in a commercial building, clinic or industrial application, aircraft, marine vessel or other transport or recreational or housing vehicle, to various equipment and processes and other locations at which the fluid is desired, such as to help sanitize the conduit sub-loops 924A-D.

A flow control valve (FCV) 922A, 922B, 922C, and 922D may be situated between ends of the conduit sub-loops 924A-D, respectively. A flow control valve regulates a flow or pressure of fluid from the continuous flow recirculating and reversing loop circuit. The flow or pressure may be specified according to the application, whether the FCV is fixed or is manually or electronically controlled. In one or more embodiments, the flow control valve regulates the flow or pressure of the fluid to a specified pressure. In this embodiment, each flow control valve 922A-D may be individually controlled by the controller, such as to individually control the pressure or flow of fluid through the flow control valve 922A-D.

When the flow control valve 922A is inhibiting or prohibiting flow of fluid therethrough, the fluid may travel through the conduit sub-loop 924A. The controller may adjust the flow of fluid using the flow reversing recirculating loop and effectively reverse the flow fluid through the conduit sub loop 924A-D.

In one or more embodiments, a cross-sectional area of a conduit 927 in the flow reversing recirculating loop circuit may be at least as big as twice a cross-sectional area of a conduit 926. Such a configuration allows for all 2WVs 904F-I to be open simultaneously and provide flow through both ends of the conduit 926 (the end between 2WV 904F and 904I and the end between 2WV 904G and 904H). Such a configuration may be helpful in situations where there is a loss of fluid pressure somewhere along the conduit loop 926. Such a loss in pressure may be detected using a sensor 933.

The sensor(s) 933 may include a pressure sensor, a flow sensor, a pH sensor, an oxidation-reduction potential sensor, or other sensor. The sensor(s) 933 may provide data to the controller indicating a condition the sensor 933 is monitoring. For example, in an embodiment in which the sensor(s) 933 includes a pressure sensor or flow sensor, the controller may open all the valves 904F-I in response to detecting a pressure that is below a threshold pressure, such as for a specified period of time. In one or more embodiments, the controller may provide a communication to personnel that maintain the system 1000 in response to determining a parameter (e.g., pH, pressure, flow, or the like) monitored by the sensor(s) 933 is above or below a specified threshold.

A flow sensor determines a volume of fluid displaced per unit time. Flow may be measured by determining a velocity of fluid over a known area or through a known volume. Alternatively, flow may be measured by determining forces produced by a flowing fluid as it overcomes a known constriction and inferring the flow rate based on the forces produced.

A pH sensor measures a concentration or activity level of hydrogen ions in an aqueous solution. The data from a pH sensor indicates how acidic or basic a solution is (an amount of free active chlorine in the solution). This data may be recorded. This data may be useful when determining the ratio of hypochlorous acid (HOCl) to hypochlorite ion (OCl-) in a given free available chlorine concentration measure, which in conjunction with contact time (CT) may be predictive of efficacy.

A pressure sensor measures an amount of force required to stop a fluid from expanding. A pressure sensor usually generates a signal based on amount of the pressure imposed thereon.

An oxidation-reduction potential (ORP) sensor measures a degree to which a substance (the fluid in the conduits) is capable of oxidizing or reducing another substance (e.g., the conduit or other substance which the fluid may contact). ORP may be measured in volts (e.g., milli-volts). A positive ORP may indicate that a substance has ORP (is an oxidizing agent).

One or more of the systems discussed herein may be used in food and beverage processing, poultry barns and milking parlors, dairies and for feed water for animal husbandry and aquaculture, and for agricultural water systems. Smaller systems may have fixed and/or portable components that may interface directly with other equipment, such as beverage equipment, such as beer and wine systems, coffee equipment, soda machines and fountains, juice systems, water and ice machines and dispensers, or the like. In one or more embodiments, the system may be used on a municipal level, such as for municipal water distribution. The parts of the system used for municipal system may be larger (in some embodiments) in diameter or maximum carrying capacity than, for example, a beverage equipment or dental system.

The system 1000 as illustrated includes a sub-sub loop 924E in fluid communication with the sub-loop 924A. A flow control valve 922E may reduce or otherwise regulate a flow of fluid therethrough. The conduit loops may be further nested, such as to include a sub-sub-sub loop may likewise be in fluid communication with the sub-sub loop 924E in the same manner that the sub-sub loop 924E is in fluid communication with the sub-loop 924A, and so on. Such embodiments may be helpful in situations, such as, for example, when a new section is added to a building, such as during a remodel or renovation, or additional point of fluid use is desired and/or needed. Adding one or more nested conduit loops may be a cost effective way to expand a distribution circuit while still ensuring a continuous fluid flow through a plumbing system.

Figure 11:
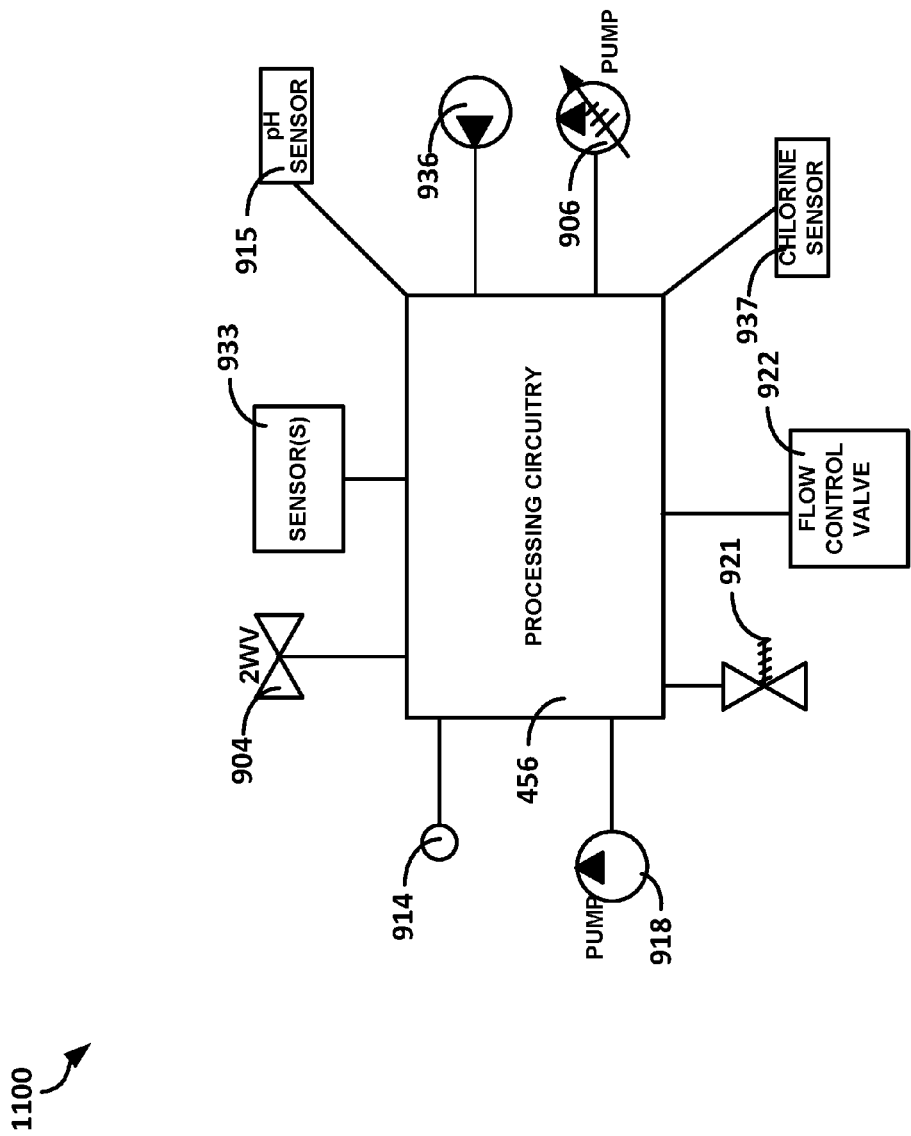
FIG. 11 illustrates, by way of example, a diagram of an embodiment of control circuitry to control one or more items of the system of FIG. 1.
Figure 13:
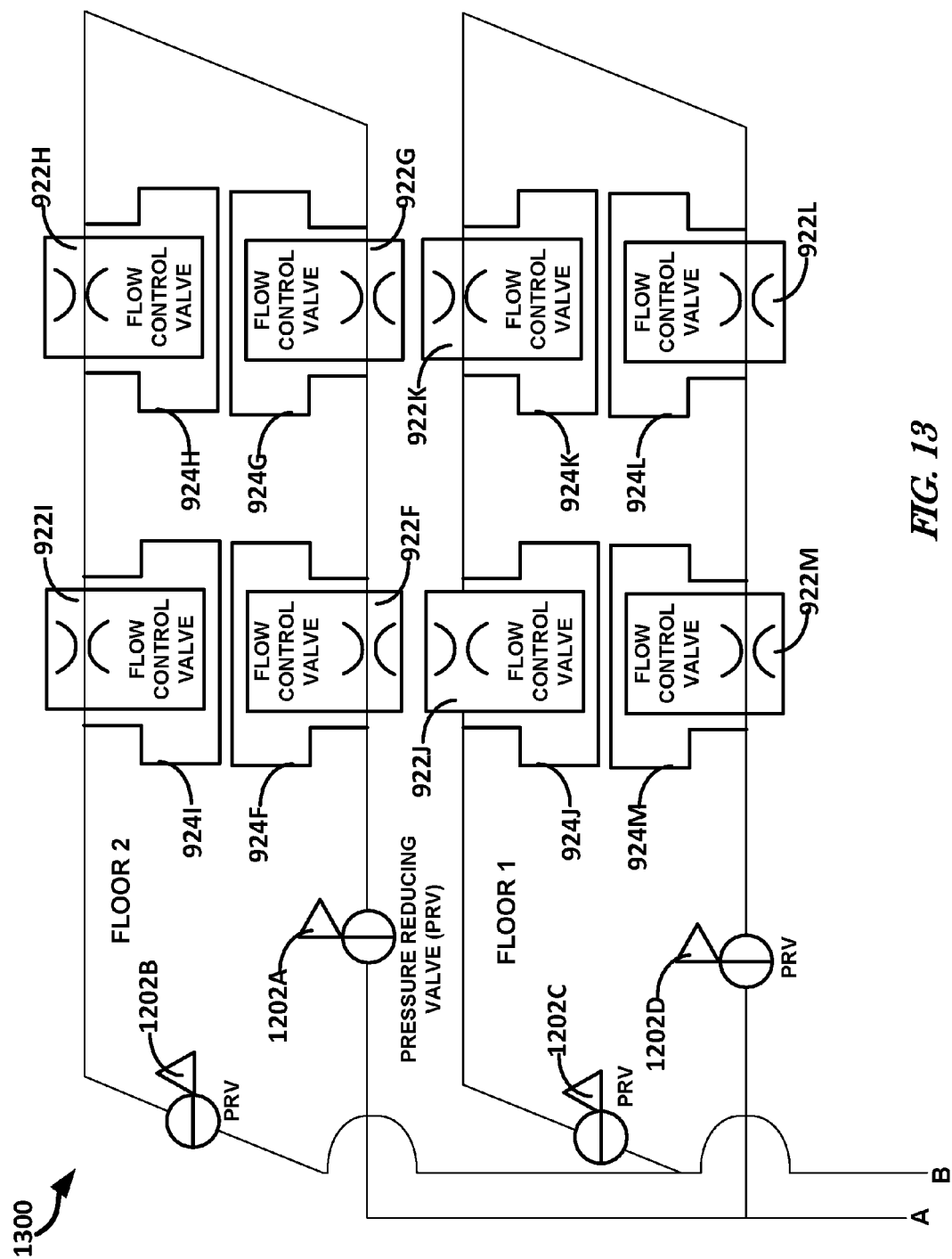
FIG. 13 illustrates, by way of example, a diagram of an embodiment of a multi-story conduit loop.

FIG. 11 illustrates, by way of example, a block diagram of an embodiment of a control system 1100, such as to control items of the system 900, 1000, and/or 1300 (see FIG. 13). The control system 1100 includes processing circuitry 456 electrically coupled, such as by a wired or wireless coupling or connection, to items of the system 1100. The processing circuitry 456 includes a hardware processor or other components (e.g., transistor(s), resistor(s), capacitor(s), regulator(s), inductor(s), Boolean logic gate(s), clock(s), multiplexer(s), state logic, memory(s), or the like) configured to receive one or more signal(s) from control of the item(s) coupled thereto. The processing circuitry 456 may perform one or more operations in response to the received signal.

The items of FIG. 11 do not include suffix reference designators so as to refer to the item more generically. Thus, for example, the 2WV 904 refers to one or more of the 2WVs 904A-904I. The operations performed by the processing circuitry 456 are performed so as to automate one or more operations of the system 900, 1000, and/or 1300.

The items illustrated as being communicatively coupled to the processing circuitry 456 include a 2WV 904 (with or without an overflow valve), a level sensor 914, a pump 908, a flow control valve 922, a pump 918, a pH sensor 938, and sensor(s) 933.

Some operations which the processing circuitry 456 may perform are now described with the understanding that this description is not exhaustive. The processing circuitry 456 may open, close, or change a position of a 2WV 904, such as by providing one or more signals to a corresponding actuator. The processing circuitry 456 may perform such opening or closing based on a time of day, a signal received from one of the sensor(s) 933, the pH sensor 938, or the level monitor 914. Similarly, the processing circuitry 456 may stop, start, or change a displacement rate of a pump 906 and/or 918 in response to one or more signals received from the sensor(s) 933, the pH sensor 938, or the level monitor 914.

The operations of the processing circuitry 456 may include:

1) Increasing or decreasing a discharge rate of the pump 906 in response to signal(s) received from the pH sensor 915.

2) Opening or closing the 2WV 904A and/or 904B in response to signal(s) received from the pH sensor 915.

3) Opening or closing the 2WV 904E in response to signal(s) received from the pH sensor 915. Using one or more of the operations 1-3, The processing circuitry 456 may keep the fluid in the tank 912 within a specified range of pHs.

4) Increasing or decreasing a flow of fluid allowed through the variable control valve 921 in response to signal(s) received from a flow sensor or pressure sensor (e.g., one of the sensor(s) 933). Such a configuration may allow for regulation of the pressure or fluid flow in the loop 926.

5) Opening or closing the 2WV 904D in response to signal(s) received from the level monitor 914, the pH sensor 915, or one of the sensor(s) 933. Such a configuration may allow for replacement of fluid in the tank 912, such as if too much biofilm or other undesirable contaminants are in the tank 912.

6) Increasing or decreasing a discharge rate of the pump 918 in response to signal(s) received from the pH sensor 915.

7) Opening or closing the 2WV(s) of the flow reversing loop (i.e. 2WVs 904F-I), such as in response to signal(s) received from the sensor(s) 933. Such a configuration allows for sanitizing of the loop 926 or for increasing an amount of fluid provided to the loop 926.

8) Opening or closing the flow control valve, such as to adjust a pressure or flow of fluid through the flow control valve 922. Such a configuration may help ensure that fluid will flow through a sub-loop 924 or will bypass the sub-loop 924.

9) Reversing a flow of fluid in response to one or more signals received from one or more of the sensor(s) 933, pH sensor 915, and/or chlorine sensor 917, such as in response to one or more signals from the one or more of the sensor(s) 933, pH sensor 915, and/or chlorine sensor 917 indicating that a characteristic (e.g., chlorine level, ORP, pH, salinity, or other characteristic) of the fluid in the system 900, 1000, and/or 1300 is greater than (or equal to) a threshold value, less than (or equal to) a threshold value, or within a specified range of values.

Figure 12:
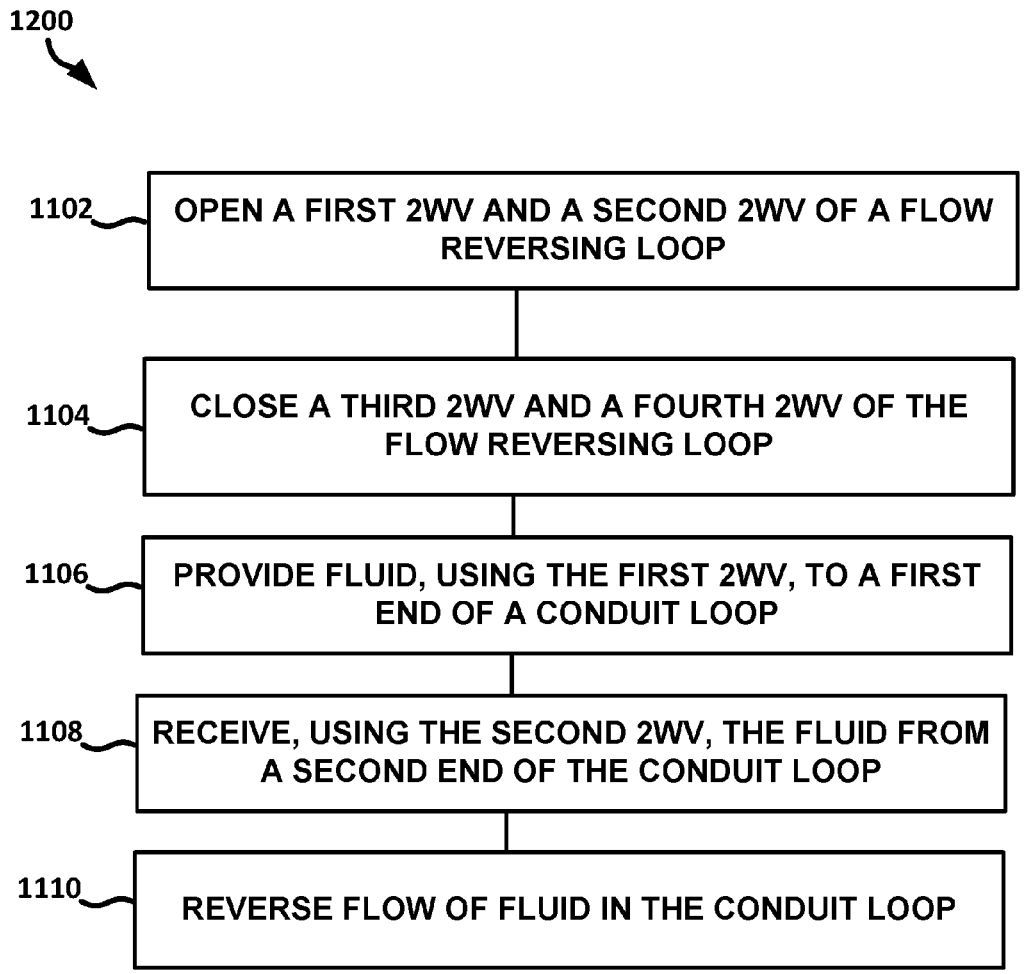
FIG. 12 illustrates, by way of example, a diagram of an embodiment of a method for reversing a flow of fluid in a conduit.

FIG. 12 illustrates, by way of example, a diagram of an embodiment of a method 1200 for reversing a flow direction of a fluid in a conduit. The method 1200 as illustrated includes: opening a first 2WV and a second 2WV of a flow reversing loop, at operation 1102; closing a third 2WV and a fourth 2WV of the flow reversing loop, at operation 1104; providing fluid, using the first 2WV, to a first end of a conduit loop, at operation 1106; receiving, using the second 2WV, the fluid from a second end of the conduit loop (the second end opposite the first end), at operation 1108; and reversing flow of the fluid in the conduit loop, at operation 1110.

In one or more embodiments, the first two-way valve may be situated between the third two-way valve and the fourth two-way valve and the second two-way valve situated between the fourth two-way valve and the third two-way valve. The operation 1110 may include opening the third two-valve and the fourth two-way valve of the flow reversing loop. The operation 1110 may include closing the first two-way valve and the second two-way valve of the flow reversing loop. The operation 1110 may include providing, using the third two-way valve, fluid from the first pump to the second end of the conduit loop. The operation 1110 may include receiving, using the fourth two-way valve, fluid from the first end of the conduit loop.

The method 1200 may further include mixing water and sanitizer in a holding tank and wherein the fluid includes the water and sanitizer mixture from the holding tank. In one or more embodiments, the sanitizer includes anolyte. The method 1200 may include adjusting a flow nozzle on a fifth two-way valve, the fifth two-way valve situated between the second two-way valve and the holding tank to adjust fluid pressure in the conduit loop. The method 1200 may further include providing fluid to a conduit sub-loop, the conduit sub-loop including a first end coupled at a first end of a flow control valve and a second end coupled at a second end of the flow control valve opposite the first end of the flow control valve. The method 1200 may further include adjusting, using the flow control valve, flow of fluid in the conduit loop.

The method 1200 may further include providing a maximum pressure and flow to each point in the loop circuit, such as may occur when every point of use and discharge in the loops circuit consumes fluid volume and pressure. Such maximum pressure and flow may be supplied by closing 2WV 904C and opening simultaneously all of the 2WV's in the reversible manifold, including 2WV's 904F, 904G, 904H and 904I. When 2WV 904C closes entirely, a signal a may be generated by the processing circuitry 456 to energize pump 936 to cause a recirculation of fluids in the mixing tank 912 to a chlorine sensor 937. In such a configuration, the chlorine sensor 937 determines free available chlorine in the fluid even when the 2WV 904C is in a closed position.

FIG. 13 illustrates, by way of example, a diagram of a system 1300 including nested conduit loops on multiple floors (stories) of a building. The labels "A" and "B" in FIG. 13 correspond to the same labels in FIGS. 9 and 10.

Fluid from the 2WV 904G may be provided to a pressure reducing valve 1202A, such as if 2WV 904G is open. A pressure reducing valve (PRV) reduces a pressure of a fluid incident thereon to a lower pressure for items downstream therefrom. The PRV 1202A reduces the pressure of fluid incident thereon allows fluid to pass to the nested loop 924F and/or the FCV 922F. Fluid may travel through the nested loop 924F, such as if the FCV 922F reduces flow therethrough to force fluid through the nested conduit loop 924F. The fluid then travels on to flow through FCV 922G and/or nested conduit loop 924G, FCV 922H and/or nested conduit loop 924H, and FCV 922I and/or nested conduit loop 924I.

In one or more embodiments, the PRVs 1202A-D may be proportional PRVs (PPRVs). Such valves are different from PRVs in that PRVs have a usually constant output pressure with a variable input pressure. In contrast PPRVs reduce the pressure of fluid at the inlet by a proportion, such as to create a non-constant output pressure with a variable input pressure. The PRVs (or PPRVs) may help maintain a narrow range of fluid pressures between two PRVs (or PPRVs).

The fluid from the nested conduit loop 924I and/or FCV 922I may be provided to another PRV 1202B, which regulates the pressure of fluid flowing to floor 1 when fluid is travelling through the system 1200 in this direction. Floor 1 is configured similar to floor 2 and fluid flows similar to that described above. Fluid may be returned to the 2WV 904I and proceed mixing tank 912 and/or the waste 916, such as in a manner described with regard to FIGS. 9 and 10.

If instead, 2WV 904F and 904H are open and 2WV 904G and 904I are closed, fluid will flow in the opposite direction through floors 1 and 2 (through PRV 2102B and 1202C first, respectively (and simultaneously), then through the FCVs and/or nested conduit loops, then through the PRV 1202A and 1202D, respectively, and returning to the system 900 through the 2WV 904I).

In one or more embodiments, the PRVs 1202A and 1202D may regulate fluid flowing therethrough to the same pressure. In one or more embodiments, the PRVs 1202B and 1202C may regulate fluid flowing therethrough to the same pressure.

As used herein a "conduit" means a hollow tubular element. The conduit can be a variety of shapes in cross-section, such as circular, rectangular, polygonal, irregular, or other shape.

In one or more embodiments, one or more of the methods, processes, and/or operations discussed herein may be performed (e.g., automatically) by a machine, a human, or a combination of machine and human interactions. An embodiment of a machine capable of performing such operations, methods, or processes is provided in FIG. 14.

Figure 14:
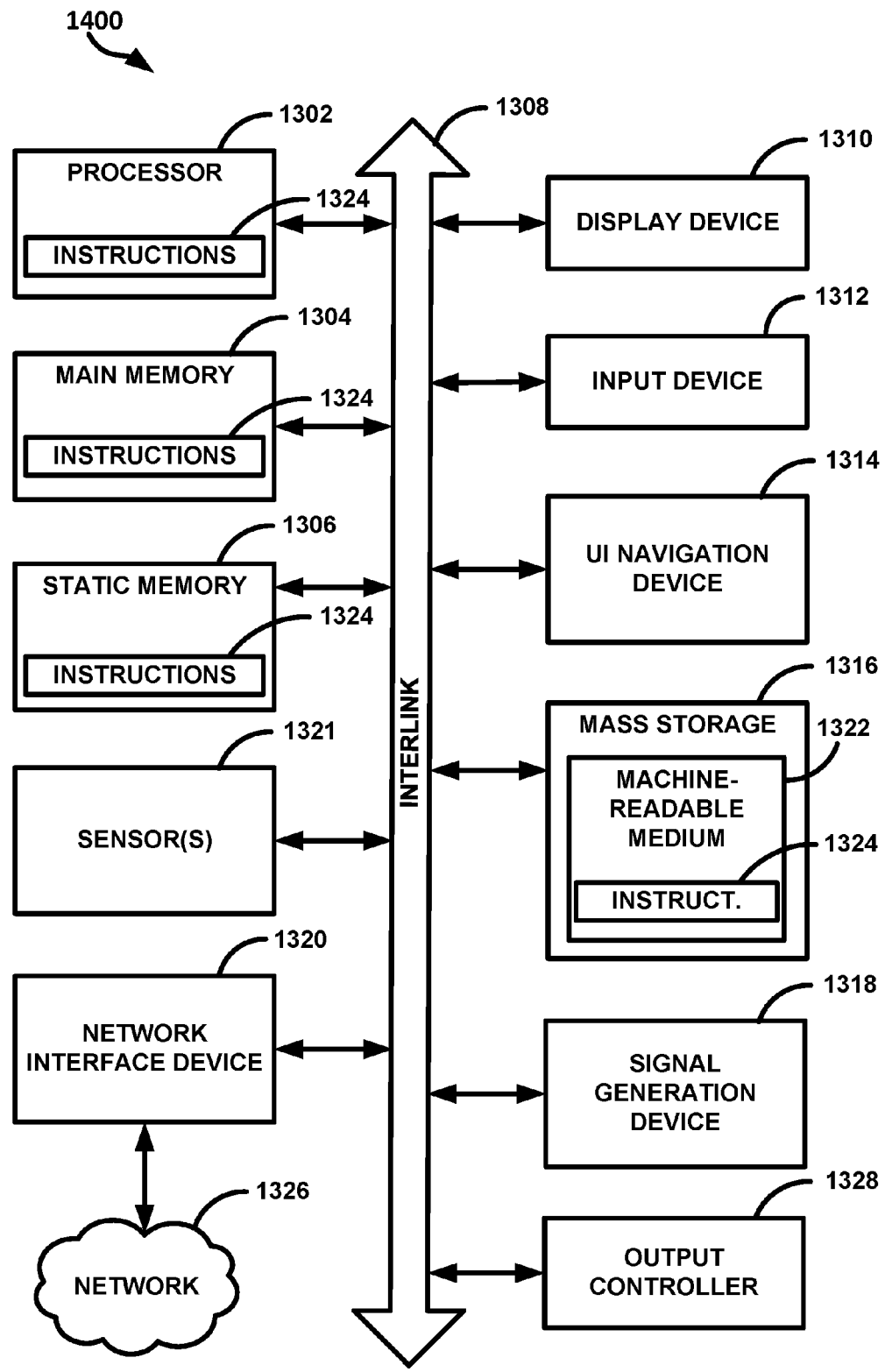
FIG. 14 illustrates, by way of example, an embodiment of a machine which may carry out one or more of the operations, methods, and/or processes discussed herein.

FIG. 14 illustrates, by way of example, an embodiment of a machine 1400 which may carry out one or more of the operations, methods, and/or processes discussed herein. In alternative embodiments, the machine 1400 operates as a standalone device or may be connected (e.g., networked) to other machines. In a networked deployment, the machine 1400 may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The machine 1400 includes a processor 1302 (e.g., a central processing unit (CPU), a graphics processing unit (GPU) or both), a main memory 1304 and a static memory 1306, which communicate with each other via a bus 1308. The computer system 1300 may further include a video display unit 1310 (e.g., a liquid crystal display (LCD) or a cathode ray tube (CRT)). The machine 1400 also includes an alphanumeric input device 1312 (e.g., a keyboard), a user interface (UI) navigation device 1314 (e.g., a mouse), a disk drive unit 1316, a signal generation device 1318 (e.g., a speaker) and a network interface device 1320.

The disk drive unit 1316 includes a machine-readable medium 1322 on which is stored one or more sets of instructions and data structures (e.g., software) 1324 embodying or utilized by any one or more of the methodologies or functions described herein. The instructions 1324 may also reside, completely or at least partially, within the main memory 1304 and/or within the processor 1302 during execution thereof by the computer system 1400, the main memory 1304 and the processor 1302 also constituting machine-readable media.

While the machine-readable medium 1322 is shown in an example embodiment to be a single medium, the term "machine-readable medium" may include a single medium or multiple media (e.g., a centralized or distributed database, and/or associated caches and servers) that store the one or more instructions or data structures. The term "machine-readable medium" shall also be taken to include any tangible medium that is capable of storing, encoding or carrying instructions for execution by the machine and that cause the machine to perform any one or more of the methodologies of the present invention, or that is capable of storing, encoding or carrying data structures utilized by or associated with such instructions. The term "machine-readable medium" shall accordingly be taken to include, but not be limited to, solid-state memories, and optical and magnetic media. Specific examples of machine-readable media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; and CD-ROM and DVD-ROM disks.

The instructions 1324 may further be transmitted or received over a communications network 1326 using a transmission medium. The instructions 1324 may be transmitted using the network interface device 1320 and any one of a number of well-known transfer protocols (e.g., HTTP). Examples of communication networks include a local area network ("LAN"), a wide area network ("WAN"), the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

EXAMPLES AND NOTES

The present subject matter may be described by way of several examples.

Example 1 may include or use subject matter (such as an apparatus, a method, a means for performing operations, or a machine readable memory including instructions that, when performed by the machine, may configure the machine to perform acts), such as may include or use a system for storage of anolyte and catholyte comprising a first pump in fluid communication with brine, the first pump to move the brine to mix with water and create diluted brine, a flow dividing valve in fluid communication with the first pump to split a stream of the diluted brine into two diluted brine streams and provide the diluted brine streams to an electrolysis device, a first catholyte tank in fluid communication with the electrolysis device to receive catholyte from the electrolysis device, a first anolyte tank in fluid communication with the electrolysis device to receive anolyte from the electrolysis device, a second catholyte tank in fluid communication with the first catholyte tank to receive catholyte from the first catholyte tank, and a second anolyte tank in fluid communication with the first anolyte tank to receive anolyte from the first anolyte tank.

Example 2 may include or use, or may optionally be combined with the subject matter of Example 1 to include or use, a first three-way valve (3WV) coupled between the pump and the flow dividing valve, wherein the first pump is in fluid communication with a first path of the 3WV and the flow dividing valve is in fluid communication with both of a first path and a second path of the 3WV, and a second pump in fluid communication with the second path of the first 3WV, the second pump moves an electrolysis device cleaning solution to the flow dividing valve through the second path of the 3WV.

Example 3 may include or use, or may optionally be combined with the subject matter of at least one of Examples 1-2 to include or use a brine tank including salt in a first well of the brine tank and water in a second well of the brine tank, the first well and the second well separated by a dividing wall that is at least partially perforated so as to allow the salt and water to mix to create the brine, and a third pump to recirculate the brine over the salt in the first well.

Example 4 may include or use, or may optionally be combined with the subject matter of at least one of Examples 1-3 to include or use a first flow control valve to regulate a flow of the water to be mixed with the brine, and one or more flow sensors in fluid communication with the water downstream from the flow control valve, the one or more flow sensors providing flow data, and the flow control valve to regulate the flow based on the flow data.

Example 5 may include or use, or may optionally be combined with the subject matter of Example 4 to include or use, wherein the first flow control valve is a pressure and temperature compensated flow control valve, and wherein the system further comprises one or more pressure sensors upstream of the first flow control valve in fluid communication with the water to determine pressure data of the water, and one or more temperature sensors upstream of the first flow control valve in fluid communication with the water to determine temperature data of the water.

Example 6 may include or use, or may optionally be combined with the subject matter of at least one of Examples 1-5 to include or use a first conductivity sensor in fluid communication with the brine upstream from the first pump, and a second conductivity sensor in fluid communication with the diluted brine downstream from the first pump.

Example 7 may include or use, or may optionally be combined with the subject matter of at least one of Examples 1-6 to include or use a second flow sensor downstream from the electrolysis device and upstream of the first catholyte tank to determine a flow rate of catholyte from the electrolysis device, and a third flow sensor downstream from the electrolysis device and upstream of the first anolyte tank to determine a flow rate of anolyte from the electrolysis device.

Example 8 may include or use, or may optionally be combined with the subject matter of Example 2 to include or use a second 3WV in fluid communication with the catholyte downstream from the electrolysis device and upstream of the first catholyte tank, wherein the first catholyte tank is in fluid communication with a first path of the second 3WV and a waste tank is in fluid communication with a second path of the second 3WV to receive the electrolysis device cleaning solution, and a third 3WV in fluid communication with the anolyte downstream from the electrolysis device and upstream of the first anolyte tank, wherein the first anolyte tank is in fluid communication with a first path of the third 3WV and the waste tank is in fluid communication with the second path of the third 3WV to receive the electrolysis device cleaning solution.

Example 9 may include or use, or may optionally be combined with the subject matter of at least one of Examples 1-8 to include or use a fourth 3WV in fluid communication with the catholyte downstream from the first catholyte tank and upstream of the second catholyte tank, wherein the second catholyte tank is in fluid communication with a first path of the fourth 3WV and a waste tank is in fluid communication with a second path of the fourth 3WV to receive catholyte from the catholyte tank, and a fifth 3WV in fluid communication with the anolyte downstream from the first anolyte tank and upstream of the second anolyte tank, wherein the second anolyte tank is in fluid communication with a first path of the fifth 3WV and the waste tank is in fluid communication with the second path of the fifth 3WV to receive anolyte from the anolyte tank.

Example 10 may include or use, or may optionally be combined with the subject matter of at least one of Examples 1-9 to include or use a fourth pump in fluid communication with catholyte from the catholyte tank to move catholyte from the catholyte tank to the anolyte tank to increase a pH of the anolyte in the anolyte tank.

Example 11 may include or use subject matter (such as an apparatus, a method, a means for performing operations, or a machine readable memory including instructions that, when performed by the machine, may configure the machine to perform acts), such as may include or use a method for storage of anolyte and catholyte comprising pumping, using a first pump, brine from a brine tank so as to mix the brine with water and create diluted brine, dividing, using a flow dividing valve in fluid communication with the first pump, a stream of the diluted brine into two diluted brine streams and providing the diluted brine streams to an electrolysis device, temporarily storing, using a first catholyte tank in fluid communication with the electrolysis device, catholyte from the electrolysis device, temporarily storing, using a first anolyte tank in fluid communication with the electrolysis device, anolyte from the electrolysis device, feeding, using a gravity feed, catholyte from the first catholyte tank to a second catholyte tank to temporarily store the catholyte therein, feeding, using a gravity feed, anolyte from the first anolyte tank to a second anolyte tank to temporarily store the anolyte therein, and providing anolyte from the anolyte tank or catholyte from a catholyte tank to an ancillary system in fluid communication with the catholyte tank and the anolyte tank.

Example 12 may include or use, or may optionally be combined with the subject matter of Example 11 to include or use pumping, using the first pump, the diluted brine solution through a first path of a first three-way valve (3WV) coupled between the first pump and the electrolysis device, and pumping, using a second pump in fluid communication with a second path of the first three-way valve (3WV), an electrolysis device cleaning solution to the flow dividing valve through the second path of the 3WV.

Example 13 may include or use, or may optionally be combined with the subject matter of at least one of Examples 11-12 to include or use mixing water and salt in a brine tank by including the salt in a first well of the brine tank and water in a second well of the brine tank and adding water to the brine tank, the first well and the second well separated by a dividing wall that is at least partially perforated so as to allow the salt and water to mix to create the brine, and recirculating, using a pump, brine over the salt in the first well.

Example 14 may include or use, or may optionally be combined with the subject matter of at least one of Examples 11-13 to include or use regulating, using a first flow control valve, a flow rate of the water to be mixed with the brine, measuring, using one or more flow sensors in fluid communication with the water downstream from the flow control valve, a flow rate of the water, wherein the flow control valve regulates the flow rate of the water based on the measured flow rate.

Example 15 may include or use, or may optionally be combined with the subject matter of Example 14 to include or use, wherein the first flow control valve is a pressure and temperature compensated flow control valve, and wherein the method further comprises determining, using one or more pressure sensors upstream of the first flow control valve and in fluid communication with the water, a pressure of the water, and determining, using one or more temperature sensors upstream of the first flow control valve and in fluid communication with the water, a temperature of the water, wherein regulating the flow rate of the water includes regulating based on the determined pressure and temperature.

Example 16 may include or use, or may optionally be combined with the subject matter of at least one of Examples 12-15 to include or use guiding, using a first path of a second 3WV in fluid communication with the catholyte downstream from the electrolysis device and upstream of the first catholyte tank, the electrolysis cleaning solution to a waste tank, guiding, using a second path of the second 3WV, the catholyte from the electrolysis device to a catholyte tank, guiding, using a first path of a third 3WV in fluid communication with the anolyte downstream from the electrolysis device and upstream of the first anolyte tank, the electrolysis cleaning solution to a waste tank, and guiding, using a second path of the third 3WV, the anolyte from the electrolysis device to an anolyte tank.

Example 17 may include or use subject matter (such as an apparatus, a method, a means for performing operations, or a machine readable memory including instructions that, when performed by the machine, may configure the machine to perform acts), such as may include or use a system for production and storage of anolyte and catholyte comprising a first pump in fluid communication with brine, the first pump to move the brine to mix with water and create diluted brine, an electrolysis device in fluid communication with the brine downstream from the first pump, a flow dividing valve in fluid communication with the first pump to split a stream of the diluted brine into two diluted brine streams and provide the diluted brine streams to the electrolysis device, a first catholyte tank in fluid communication with the electrolysis device to receive catholyte from the electrolysis device, a first anolyte tank in fluid communication with the electrolysis device to receive anolyte from the electrolysis device, a second catholyte tank in fluid communication with the first catholyte tank to receive catholyte from the catholyte tank, and a second anolyte tank in fluid communication with the first anolyte tank to receive anolyte from the anolyte tank.

Example 18 may include or use, or may optionally be combined with the subject matter of Example 17 to include or use a brine tank including salt in a first well of the brine tank and water in a second well of the brine tank, the first well and the second well separated by a dividing wall that is at least partially perforated so as to allow the salt and water to mix to create the brine, and a second pump to recirculate the brine over the salt in the first well.

Example 19 may include or use, or may optionally be combined with the subject matter of at least one of Examples 17-18 to include or use an ancillary system comprising a third pump in fluid communication with catholyte from the second catholyte tank and a fourth pump in fluid communication with anolyte from the second anolyte tank, the third pump to move catholyte from the catholyte tank to a holding tank of the ancillary system and the fourth pump to move anolyte from the anolyte tank to the holding tank.

Example 20 may include or use, or may optionally be combined with the subject matter of at least one of Examples 17-19 to include or use a first three-way valve (3WV) coupled between the first pump and the flow dividing valve, the first 3WV including a first path and a second path therethrough, wherein the flow dividing valve is in fluid communication with both the first and the second paths, and wherein the first pump is in fluid communication with the first path, a tank for holding electrolysis device cleaning solution in fluid communication with the first path, and a second pump in fluid communication with the second path of the first 3WV, the second pump moves the electrolysis device cleaning solution to the flow dividing valve through the second path of the 3WV.

Example 21 may include or use subject matter (such as an apparatus, a method, a means for performing operations, or a machine readable memory including instructions that, when performed by the machine, may configure the machine to perform acts), such as may include or use a method of cleaning and sanitizing an internal or external surface of an object, the method comprising treating the surface with a cleaning solution to create a treated surface, measuring, using a luminometer, an amount of adenosine triphosphate (ATP) on the treated surface, determining whether the measured amount of ATP is less than a specified threshold amount of ATP, and treating the treated surface with a sanitizing solution in response to a determination that the amount of ATP is less than the specified threshold amount of ATP.

Example 22 may include or use, or may optionally be combined with the subject matter of Example 21 to include or use, wherein the cleaning solution includes catholyte.

Example 23 may include or use, or may optionally be combined with the subject matter of at least one of Examples 21-22 to include or use, wherein the sanitizing solution includes anolyte.

Example 24 may include or use, or may optionally be combined with the subject matter of at least one of Examples 22-23 to include or use, wherein the catholyte and the anolyte are produced at least in part using catholyte and anolyte from an electrolysis cell.

Example 25 may include or use, or may optionally be combined with the subject matter of Example 24 to include or use, wherein the catholyte and anolyte from the electrolysis cell are produces using water that includes less than one part per million of each of hardness, fluoride, iron, magnesium, and borax and borate.

Example 26 may include or use, or may optionally be combined with the subject matter of at least one of Examples 21-25 to include or use performing a process validation process to determine a contact time for which the cleaning solution is to be present on the contact surface, pH of the cleaning solution, concentration of the cleaning solution, and the threshold value.

Example 27 may include or use, or may optionally be combined with the subject matter of Example 26 to include or use, wherein treating the surface with a cleaning solution to create a treated surface includes treating the surface with the cleaning solution in accord with the contact time, pH of the cleaning solution, cleaning solution concentration, and the threshold value.

Example 28 may include or use, or may optionally be combined with the subject matter of at least one of Examples 21-27 to include or use performing a process validation process to determine a contact time for which the sanitizing solution is to be present on the contact surface, pH of the sanitizing solution, and sanitizing solution concentration.

Example 29 may include or use, or may optionally be combined with the subject matter of Example 28 to include or use, wherein treating the treated surface includes treating the treated surface with the sanitizing solution in accord with the determined contact time, pH of the sanitizing solution, and sanitizing solution concentration.

Example 30 may include or use, or may optionally be combined with the subject matter of at least one of Examples 26-29 to include or use diluting catholyte from the electrolysis cell to the determined concentration and pH to create the cleaning solution.

Example 31 may include or use, or may optionally be combined with the subject matter of at least one of Examples 26-30 to include or use, wherein the pH is between about 10.3 and 11.3 or 13.5.

Example 32 may include or use, or may optionally be combined with the subject matter of at least one of Examples 21-31 to include or use diluting anolyte to the determined specified concentration and pH to create the sanitizing solution.

Example 33 may include or use, or may optionally be combined with the subject matter of at least one of Examples 21-32 to include or use re-treating the surface with the cleaning solution in response to a determination that the measured of amount of ATP is not less than (or equal to) the specified threshold amount of ATP.

Example 34 may include or use, or may optionally be combined with the subject matter of at least one of Examples 21-33 to include or use, wherein treating the surface with a cleaning solution to create a treated surface includes using an emulsifier and a catholyte solution.

Example 35 may include or use, or may optionally be combined with the subject matter of at least one of Examples 21-34 to include or use, wherein treating the surface with a cleaning solution to create a treated surface includes using a kinetic agent to increase the effectiveness of the catholyte solution.

Example 36 may include or use, or may optionally be combined with the subject matter of Example 35 to include or use, wherein the kinetic agent includes one or more of heating a temperature of the surface or the cleaning solution and scrubbing the cleaning solution into the surface.

Example 37 may include or use, a non-transitory machine-readable storage device including instructions stored thereon which, when executed by the machine, cause the machine to perform operations comprising the method of one or more of the Examples 21-36.

Example 38 may include or use subject matter (such as an apparatus, a method, a means for performing operations, or a machine readable memory including instructions that, when performed by the machine, may configure the machine to perform acts), such as may include or use a first pump in fluid communication with a fluid, a flow reversing loop circuit comprising a first two-way valve, a second two-way valve, a third two-way valve, and a fourth two-way valve, the first and second two-way valves in fluid communication with fluid from the first pump, and a conduit loop circuit including a first end in fluid communication with the second and third two-way valves and a second end opposite the first end in fluid communication with the first and fourth two-way valves, the flow reversing loop circuit configured such that when the first and third two-way valves are open and the second and fourth two-way valves are closed fluid from the first two-way valve flows to the second end of the conduit loop, flows through the conduit loop to the first end of the conduit loop, and flows to the drain through the third two-way valve, and when the second and fourth two-way valves are open and the first and third two-way valves are closed fluid from the second two-way valve flows to the first end of the conduit loop, flows through conduit loop to the second end of the conduit loop, and flows to the drain through the fourth two-way valve.

Example 39 may include or use, or may optionally be combined with the subject matter of Example 38 to include or use, a water inlet, a treatment agent inlet, and a holding and mixing tank to receive water from the water inlet and treatment agent from the treatment agent inlet, the holding and mixing tank in fluid communication with the first pump, the fluid including a mix of the water and treatment agent.

Example 40 may include or use, or may optionally be combined with the subject matter of Example 39 to include or use a second pump in fluid communication with the treatment agent inlet in fluid communication with the treatment agent.

Example 41 may include or use, or may optionally be combined with the subject matter of at least one of Examples 39-40 to include or use a fifth two-way valve situated between the check valve and the holding tank.

Example 42 may include or use, or may optionally be combined with the subject matter of Example 41 to include or use a sixth two-way valve situated between the fifth two-way valve and the holding tank and the sixth two-valve situated between the flow reversing loop and the holding tank, the sixth two-way valve including a variable flow nozzle to help ensure sufficient pressure of fluid in the flow reversing loop and the conduit loop.

Example 43 may include or use, or may optionally be combined with the subject matter of at least one of Examples 39-42 to include or use a sensor in fluid communication with the fluid in the tank to measure free active chlorine or pH of the fluid.

Example 44 may include or use, or may optionally be combined with the subject matter of at least one of Examples 39-43 to include or use a seventh two-way valve situated between the water inlet and the holding tank.

Example 45 may include or use, or may optionally be combined with the subject matter of at least one of Examples 39-44 to include or use, wherein the treatment agent includes anolyte.

Example 46 may include or use, or may optionally be combined with the subject matter of at least one of Examples 38-45 to include or use an expansion tank between the first pump and the flow reversing loop.

Example 47 may include or use, or may optionally be combined with the subject matter of at least one of Examples 38-46 to include or use one or more conduit sub-loops in fluid communication with the conduit loop.

Example 48 may include or use, or may optionally be combined with the subject matter of Example 47 to include or use a flow control valve for each of the one or more conduit sub-loops, each flow control valve situated between a first end of a respective conduit sub-loop and a second end of the respective conduit sub-loop opposite the first end of the respective conduit sub-loop.

Example 49 may include or use subject matter (such as an apparatus, a method, a means for performing operations, or a machine readable memory including instructions that, when performed by the machine, may configure the machine to perform acts), such as may include or use opening a first two-valve and a second two-way valve of a flow reversing loop, closing a third two-way valve and a fourth two-way valve of the flow reversing loop, the first two-way valve situated between the third two-way valve and the fourth two-way valve, the second two-way valve situated between the fourth two-way valve and the third two-way valve, providing, using the first two-way valve, fluid to a first end of a conduit loop, and receiving, using the second two-way valve, fluid from a second end of the conduit loop opposite the first end of the conduit loop, reversing flow of fluid in the conduit loop including opening the third two-valve and the fourth two-way valve of the flow reversing loop, closing the first two-way valve and the second two-way valve of the flow reversing loop, providing, using the third two-way valve, fluid from the first pump to the second end of the conduit loop, and receiving, using the fourth two-way valve, fluid from the first end of the conduit loop.

Example 50 may include or use, or may optionally be combined with the subject matter of Example 49 to include or use mixing water and treatment agent in a holding tank and wherein the fluid includes the water and treatment agent mixture from the holding tank.

Example 51 may include or use, or may optionally be combined with the subject matter of Example 47 to include or use, wherein the treatment agent includes anolyte.

Example 52 may include or use, or may optionally be combined with the subject matter of at least one of Examples 49-51 to include or use adjusting a flow nozzle on a fifth two-way valve situated between the second two-way valve and the holding tank to adjust fluid pressure in the conduit loop.

Example 53 may include or use, or may optionally be combined with the subject matter of Example 52 to include or use providing fluid to a conduit sub-loop, the conduit sub-loop including a first end coupled at a first end of a flow control valve and a second end coupled at a second end of the flow control valve opposite the first end of the flow control valve; and adjusting, using the fifth two-way valve, flow of fluid in the conduit loop.

Example 54 may include or use subject matter (such as an apparatus, a method, a means for performing operations, or a machine readable memory including instructions that, when performed by the machine, may configure the machine to perform acts), such as may include or use a water inlet, a treatment agent inlet, a holding tank to receive water from the water and treatment agent from the treatment agent inlet and provide a medium in which to mix the water and treatment agent to create a fluid, a first pump in fluid communication with the fluid, a flow reversing loop comprising a first two-way valve, a second two-way valve, a third two-way valve, and a fourth two-way valve, the first and second two-way valves in fluid communication with fluid from the first pump, a conduit loop including a first end in fluid communication with the second and third two-way valves and a second end opposite the first end in fluid communication with the first and fourth two-way valves, and one or more conduit sub-loops in fluid communication with the conduit loop, the flow reversing loop configured such that when the first and third two-way valves are open and the second and fourth two-way valves are closed fluid from the first two-way valve flows to the second end of the conduit loop, flows through the conduit loop to the first end of the conduit loop, and flows to the drain through the third two-way valve, and when the second and fourth two-way valves are open and the first and third two-way valves are closed fluid from the second two-way valve flows to the first end of the conduit loop, flows through conduit loop to the second end of the conduit loop, and flows to the drain through the fourth two-way valve.

Example 55 may include or use, or may optionally be combined with the subject matter of Example 54 to include or use a fifth two-way valve situated between the flow reversing loop and the holding tank, the fifth two-way valve including a variable flow nozzle to alter fluid pressure in the flow reversing loop and the conduit loop, a chlorine sensor in fluid communication with fluid from the fifth two way valve, and processing circuitry to, in response to determining the variable flow nozzle is closed, activate a second pump in fluid communication with the fluid from the fifth two way valve and recirculate fluid from the mixing tank to the chlorine sensor.

Example 56 may include or use, or may optionally be combined with the subject matter of at least one of Examples 54-55 to include or use a flow control valve for each of the one or more conduit sub-loops, each flow control valve situated between a first end of a respective conduit sub-loop and a second end of the respective conduit sub-loop opposite the first end of the respective conduit sub-loop.

Example 57 may include or use, or may optionally be combined with the subject matter of at least one of Examples 54-56 to include or use, wherein the treatment agent includes anolyte and the system further comprises an expansion tank between the first pump and the flow reversing loop.

Example 58 may include or use, or may optionally be combined with the subject matter of at least one of Examples 54-57 to include or use two or more pressure reducing valves (PRVs) or proportional pressure reducing valves (PPRV's) on two separate floors of a building, one of the PRVs or PPRVs near a first end of a nested conduit loop on a floor of the floors and another of the PRVs or PPRVs near a second end of the nested conduit loop, the first end opposite the second end.

Example 59 may include or use subject matter (such as an apparatus, a method, a means for performing operations, or a machine readable memory including instructions that, when performed by the machine, may configure the machine to perform acts), such as may include or use a system for providing a treatment agent to one or more locations, comprising a flow reversing loop having an inlet to receive a fluid, an outlet in communication with a drain, a first port on a first side of the flow reversing loop, and a second port on a second side of the flow reversing loop, the first and second sides separated by the inlet and outlet, a conduit loop including a first end in fluid communication with the first port of the flow reversing loop and a second end in communication with the second port of the flow reversing loop, the conduit loop including one or more flow paths to the one or more location, wherein the flow reversing loop includes a first flow path from the inlet to the first port so that the treatment fluid can flow through the conduit loop in a first direction from the first end of the conduit loop to the second end of the conduit loop and to the outlet of the flow reversing loop, and a second flow path from the inlet to the second port so that the treatment fluid can flow through the conduit loop in a second direction, opposite of the first direction, from the second end of the conduit loop to the first end of the conduit loop and to the outlet of the flow reversing loop.

Example 60 may include or use, or may optionally be combined with the subject matter of Example 59 to include or use a first pump in fluid communication with the fluid to provide the fluid to the inlet.

Example 61 may include or use, or may optionally be combined with the subject matter of at least one of Examples 59-60 to include or use, wherein the flow reversing loop includes a first two-way valve, a second two-way valve, a third two-way valve, and a fourth two-way valve, the first and second two-way valves in fluid communication with fluid from the first pump, wherein, when the first and third two-way valves are open and the second and fourth two-way valves are closed fluid from the first two-way valve flows to the second end of the conduit loop, flows through the conduit loop to the first end of the conduit loop, and flows to a drain through the third two-way valve, and when the second and fourth two-way valves are open and the first and third two-way valves are closed fluid from the second two-way valve flows to the first end of the conduit loop, flows through conduit loop to the second end of the conduit loop, and flows to the drain through the fourth two-way valve.

Example 62 may include or use, or may optionally be combined with the subject matter of at least one of Examples 59-61 to include or use a water inlet, a treatment agent inlet, and a holding and mixing tank to receive water from the water inlet and treatment agent from the treatment agent inlet, the holding mixing tank in fluid communication with the inlet of the flow reversing loop, the fluid including a mix of the water and treatment agent.

Example 63 may include or use, or may optionally be combined with the subject matter of at least one of Examples 62 to include or use a second pump in fluid communication with the treatment agent inlet.

Example 64 may include or use, or may optionally be combined with the subject matter of at least one of Examples 62-63 to include or use a fifth two-way valve situated between a check valve and the holding tank.

Example 65 may include or use, or may optionally be combined with the subject matter of Example 64 to include or use a sixth two-way valve situated between the fifth two-way valve and the holding tank and the sixth two-way valve situated between the flow reversing loop and the holding tank, the sixth two-way valve including a variable flow nozzle to help ensure sufficient pressure of fluid in the flow reversing loop and the conduit loop.

Example 66 may include or use, or may optionally be combined with the subject matter of at least one of Examples 59-65 to include or use a sensor in fluid communication with fluid between the outlet and the drain to measure one or more of free active chlorine, pH, and oxidation-reduction potential (ORP) of the fluid.

Example 67 may include or use, or may optionally be combined with the subject matter of Example 65 to include or use a seventh two-way valve situated between the water inlet and the holding tank.

Example 68 may include or use, or may optionally be combined with the subject matter of at least one of Examples 59-67 to include or use, wherein the fluid includes anolyte.

Example 69 may include or use, or may optionally be combined with the subject matter of at least one of Examples 59-68 to include or use an expansion tank between a first pump and the flow reversing loop.

Example 70 may include or use, or may optionally be combined with the subject matter of at least one of Examples 59-69 to include or use one or more conduit sub-loops in fluid communication with the conduit loop.

Example 71 may include or use, or may optionally be combined with the subject matter of at least one of Example 70 to include or use a flow restricter valve for each of the one or more conduit sub-loops, each flow control valve situated between a first end of a respective conduit sub-loop and a second end of the respective conduit sub-loop opposite the first end of the respective conduit sub-loop.

Example 72 may include or use, or may optionally be combined with the subject matter of at least one of Examples 59-71 to include or use one or more sensors between the flow reversing loop and the drain, and a controller to receive signals from the one or more sensors and reverse the flow of fluid through the flow reversing loop based on the received signals.

Example 73 may include or use, or may optionally be combined with the subject matter of at least one of Examples 59-71 to include or use a controller coupled to the flow reversing loop to periodically reverse the flow of fluid through the low reversing loop.

Each of these non-limiting examples may stand on its own, or may be combined in various permutations or combinations with one or more of the other examples.

The above detailed description includes references to the accompanying drawings, which form a part of the detailed description. The drawings show, by way of illustration, specific embodiments in which methods, apparatuses, and systems discussed herein may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

What is claimed is:

1. A system for providing a fluid to one or more locations, comprising:
   a water inlet;
   a treatment agent inlet;
   a holding and mixing tank to receive water from the water inlet and treatment agent from the treatment agent inlet, the holding and mixing tank in fluid communication with an inlet of a flow reversing loop, a fluid including a mix of the water and treatment agent;

a first pump in fluid communication with the treatment agent inlet;

the flow reversing loop having the inlet to receive the fluid, an outlet in communication with a drain, a first port on a first side of the flow reversing loop, and a second port on a second side of the flow reversing loop, the first and second sides separated by the inlet and outlet;

a conduit loop including a first end in fluid communication with the first port of the flow reversing loop and a second end in communication with the second port of the flow reversing loop, the conduit loop including one or more flow paths to the one or more locations;

wherein the flow reversing loop includes:

a first flow path from the inlet to the first port so that the fluid can flow through the conduit loop in a first direction from the first end of the conduit loop to the second end of the conduit loop and to the outlet of the flow reversing loop;

a second flow path from the inlet to the second port so that the treatment fluid can flow through the conduit loop in a second direction, opposite of the first direction, from the second end of the conduit loop to the first end of the conduit loop and to the outlet of the flow reversing loop; and a first two-way valve, a second two-way valve, a third two-way valve, and a fourth two-way valve, the first and second two-way valves in fluid communication with fluid from a second pump, wherein, when the first and third two-way valves are open and the second and fourth two-way valves are closed fluid from the first two-way valve flows to the second end of the conduit loop, flows through the conduit loop to the first end of the conduit loop, and flows to the drain through the third two-way valve, and when the second and fourth two-way valves are open and the first and third two-way valves are closed fluid from the second two-way valve flows to the first end of the conduit loop, flows through conduit loop to the second end of the conduit loop, and flows to the drain through the fourth two-way valve;

a fifth two-way valve situated between a check valve and the holding and mixing tank; and a sixth two-way valve situated between the fifth two-way valve and the holding and mixing tank and the sixth two-way valve situated between the flow reversing loop and the holding and mixing tank, the sixth two-way valve including a variable flow nozzle to help ensure sufficient pressure of fluid in the flow reversing loop and the conduit loop.

2. The system of claim 1, further comprising a sensor in fluid communication with fluid between the outlet and the drain to measure one or more of free active chlorine, pH, and oxidation-reduction potential (ORP) of the fluid.

3. The system of claim 2, further comprising a seventh two-way valve situated between the water inlet and the holding and mixing tank.

4. The system of claim 1, further comprising the second pump in fluid communication with the fluid to provide the fluid to the inlet.

5. The system of claim 1, wherein the fluid includes anolyte.

6. The system of claim 1, further comprising an expansion tank between the second pump and the flow reversing loop.

7. The system of claim 1, further comprising one or more conduit sub-loops in fluid communication with the conduit loop.

8. The system of claim 7, further comprising a flow restricter valve for each of the one or more conduit sub-loops, each flow control valve situated between a first end of a respective conduit sub-loop and a second end of the respective conduit sub-loop opposite the first end of the respective conduit sub-loop.

9. The system of claim 1, further comprising:
one or more sensors between the flow reversing loop and the drain; and
a controller to receive signals from the one or more sensors and reverse the flow of fluid through the flow reversing loop based on the received signals.

10. The system of claim 1, further comprising:
a controller coupled to the flow reversing loop to periodically reverse the flow of fluid through the flow reversing loop.

* * * * *